United States Patent
Hu et al.

(10) Patent No.: US 10,182,947 B2
(45) Date of Patent: Jan. 22, 2019

(54) PRESSURE INDICATOR

(75) Inventors: Dean Hu, San Leandro, CA (US); Kenton Fong, Mountain View, CA (US); Moshe Pinto, Mountain View, CA (US); Philip Hui, Foster City, CA (US); Kenneth Wu, San Francisco, CA (US); Craig McGreevy, Walnut Creek, CA (US); Evan Anderson, San Francisco, CA (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 13/030,042

(22) Filed: Feb. 17, 2011

(65) Prior Publication Data

US 2011/0137270 A1    Jun. 9, 2011

Related U.S. Application Data

(63) Continuation of application No. 12/626,426, filed on Nov. 25, 2009, now abandoned.
(Continued)

(51) Int. Cl.
*A61F 13/02* (2006.01)
*A61M 1/00* (2006.01)
*A61F 13/00* (2006.01)

(52) U.S. Cl.
CPC .... *A61F 13/0213* (2013.01); *A61F 13/00051* (2013.01); *A61F 13/00068* (2013.01);
(Continued)

(58) Field of Classification Search
USPC .............. 602/54, 43; 604/289, 304–308
See application file for complete search history.

(56) References Cited

U.S. PATENT DOCUMENTS

| 406,330 | A | 7/1889 | Austin |
| 418,469 | A | 12/1889 | Mckinly |

(Continued)

FOREIGN PATENT DOCUMENTS

| AU | 550575 B2 | 3/1986 |
| AU | 745271 B2 | 3/2002 |

(Continued)

OTHER PUBLICATIONS

US 7,186,244, 03/2007, Hunt et al. (withdrawn)
(Continued)

*Primary Examiner* — Ophelia A Hawthorne
*Assistant Examiner* — Caitlin Carreiro

(57) ABSTRACT

Disclosed herein is a device which is intended to deliver and maintain reduced pressure to body surfaces for application of reduced pressure wound therapy (RPWT) also known as negative pressure wound therapy (NPWT). During application of this type of therapy, a substantially airtight seal is formed around a section of tissue to be treated. This seal is formed by a dressing which provides fluid communication from a section of tissue to a reduced pressure source. Disclosed herein is a dressing system which is configured to enhance usability and functionality of this dressing. First, the system may be configured to allow full rotation of the fluid communication conduit to the reduced pressure source along the axis substantially normal to the dressing. Second, the system may be configured to include a one-way valve to prevent backflow of any drainage fluids. Third, the system may be configured with transparent windows covered by opaque flaps to allow inspection through the dressing. Fourth, the system may be configured to include an indicator which visually makes clear whether reduced pressure is being applied or not. Fifth, the system is configured to minimize the profile of the dressing system.

27 Claims, 24 Drawing Sheets

Related U.S. Application Data

(60) Provisional application No. 61/117,921, filed on Nov. 25, 2008, provisional application No. 61/117,920, filed on Nov. 25, 2008.

(52) U.S. Cl.
CPC ........ *A61F 13/022* (2013.01); *A61F 13/0216* (2013.01); *A61F 13/0223* (2013.01); *A61F 13/0253* (2013.01); *A61F 13/0256* (2013.01); *A61M 1/0027* (2014.02); *A61M 1/0088* (2013.01); *A61F 2013/00412* (2013.01)

(56) References Cited

U.S. PATENT DOCUMENTS

| | | |
|---|---|---|
| 617,936 A | 1/1899 | Nicolas |
| 1,355,846 A | 10/1920 | Rannells |
| 2,198,666 A | 4/1940 | Gruskin |
| 2,306,107 A | 12/1942 | Henderson |
| 2,472,116 A | 6/1949 | Maynes |
| 2,523,850 A | 9/1950 | Steinberg |
| 2,547,758 A | 4/1951 | Keeling |
| 2,632,443 A | 3/1953 | Lesher |
| 2,660,342 A | 11/1953 | Ruf |
| 2,682,873 A | 7/1954 | Evans et al. |
| 2,863,452 A | 12/1958 | Ogle, Sr. |
| 2,910,763 A | 11/1959 | Lauterbach |
| 2,969,057 A | 1/1961 | Simmons |
| 3,066,672 A | 12/1962 | Crosby, Jr. et al. |
| 3,073,309 A | 1/1963 | Mosier |
| 3,334,628 A | 8/1967 | Saemann et al. |
| 3,367,332 A | 2/1968 | Groves |
| 3,401,522 A | 9/1968 | Hann et al. |
| 3,520,300 A | 7/1970 | Flower, Jr. |
| 3,568,675 A | 3/1971 | Harvey |
| 3,583,399 A | 6/1971 | Ritsky |
| 3,628,325 A | 12/1971 | Morita |
| 3,648,692 A | 3/1972 | Wheeler |
| 3,680,560 A | 8/1972 | Pannier, Jr. et al. |
| 3,682,180 A | 8/1972 | McFarlane |
| 3,750,393 A | 8/1973 | Minto et al. |
| 3,779,243 A | 12/1973 | Tussey et al. |
| 3,809,086 A | 5/1974 | Schachet et al. |
| 3,809,087 A | 5/1974 | Lewis, Jr. |
| 3,826,254 A | 7/1974 | Mellor |
| 3,833,030 A | 9/1974 | Waldbauer, Jr. et al. |
| 3,841,331 A | 10/1974 | Wilder et al. |
| 3,864,766 A | 2/1975 | Prete, Jr. |
| 3,958,570 A | 5/1976 | Vogelman et al. |
| 3,982,546 A | 9/1976 | Friend |
| 4,041,934 A | 8/1977 | Genese |
| 4,067,330 A | 1/1978 | Roache |
| 4,080,970 A | 3/1978 | Miller |
| 4,096,853 A | 6/1978 | Weigand |
| 4,124,116 A | 11/1978 | McCabe, Jr. |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,278,089 A | 7/1981 | Huck et al. |
| 4,284,079 A | 8/1981 | Adair |
| 4,287,819 A | 9/1981 | Emerit |
| 4,297,995 A | 11/1981 | Golub |
| 4,333,456 A | 6/1982 | Webb |
| 4,333,458 A | 6/1982 | Margulies et al. |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,404,924 A | 9/1983 | Goldberg et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,484,919 A | 11/1984 | Sohn et al. |
| 4,525,166 A | 6/1985 | Leclerc |
| 4,525,167 A | 6/1985 | Goldberg et al. |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,549,554 A | 10/1985 | Markham |
| 4,551,139 A | 11/1985 | Plaas et al. |
| 4,569,348 A | 2/1986 | Hasslinger |
| 4,569,674 A | 2/1986 | Phillips et al. |
| 4,578,060 A | 3/1986 | Huck et al. |
| 4,605,399 A | 8/1986 | Weston et al. |
| 4,608,041 A | 8/1986 | Nielsen |
| 4,640,688 A | 2/1987 | Hauser |
| 4,648,870 A | 3/1987 | Goldberg et al. |
| 4,655,754 A | 4/1987 | Richmond et al. |
| 4,664,128 A | 5/1987 | Lee |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,747,960 A | 5/1988 | Freeman et al. |
| 4,758,220 A | 7/1988 | Sundblom et al. |
| 4,758,232 A | 7/1988 | Chak |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,867,748 A | 9/1989 | Samuelsen |
| 4,872,450 A | 10/1989 | Austad |
| 4,878,901 A | 11/1989 | Sachse |
| 4,882,337 A | 11/1989 | Sweet et al. |
| 4,889,250 A | 12/1989 | Beyer |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,018,516 A | 5/1991 | Gilman |
| 5,037,397 A | 8/1991 | Kalt et al. |
| 5,071,409 A | 12/1991 | Rosenberg |
| 5,073,172 A | 12/1991 | Fell |
| 5,086,170 A | 2/1992 | Luheshi et al. |
| 5,092,858 A | 3/1992 | Benson et al. |
| 5,100,396 A | 3/1992 | Zamierowski |
| 5,107,859 A | 4/1992 | Alcorn et al. |
| 5,116,310 A | 5/1992 | Seder et al. |
| 5,116,610 A | 5/1992 | Broaddus |
| 5,133,821 A | 7/1992 | Jensen |
| 5,134,994 A | 8/1992 | Say |
| 5,149,331 A | 9/1992 | Ferdman et al. |
| 5,154,697 A | 10/1992 | Loori |
| 5,157,808 A | 10/1992 | Sterner, Jr. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,263,922 A | 11/1993 | Soya et al. |
| 5,266,476 A | 11/1993 | Sussman et al. |
| 5,278,100 A | 1/1994 | Doan et al. |
| 5,279,550 A | 1/1994 | Habib et al. |
| 5,284,621 A | 2/1994 | Kaufman |
| 5,298,015 A | 3/1994 | Komatsuzaki et al. |
| 5,342,376 A | 8/1994 | Ruff |
| 5,344,415 A | 9/1994 | DeBusk et al. |
| 5,356,372 A | 10/1994 | Donovan et al. |
| 5,358,494 A | 10/1994 | Svedman |
| 5,380,295 A | 1/1995 | Vacca |
| 5,395,345 A | 3/1995 | Gross |

(56) References Cited

U.S. PATENT DOCUMENTS

| | | |
|---|---|---|
| 5,437,622 A | 8/1995 | Carion |
| 5,437,651 A | 8/1995 | Todd et al. |
| 5,527,293 A | 6/1996 | Zamierowski |
| 5,531,999 A | 7/1996 | Cartmell et al. |
| 5,549,584 A | 8/1996 | Gross |
| 5,556,375 A | 9/1996 | Ewall |
| 5,584,801 A | 12/1996 | Kuroyanagi et al. |
| 5,607,388 A | 3/1997 | Ewall |
| 5,636,643 A | 6/1997 | Argenta et al. |
| 5,645,081 A | 7/1997 | Argenta et al. |
| H1687 H | 10/1997 | Roe et al. |
| 5,701,917 A | 12/1997 | Khouri |
| 5,704,905 A | 1/1998 | Jensen et al. |
| 5,711,969 A | 1/1998 | Patel et al. |
| 5,845,641 A | 12/1998 | Pinney et al. |
| 5,961,497 A | 10/1999 | Larkin |
| 5,970,979 A | 10/1999 | Christofel et al. |
| 6,071,267 A | 6/2000 | Zamierowski |
| 6,135,116 A | 10/2000 | Vogel et al. |
| 6,142,982 A | 11/2000 | Hunt et al. |
| 6,174,306 B1 | 1/2001 | Fleischmann |
| 6,211,426 B1 | 4/2001 | Abrams |
| 6,235,964 B1 | 5/2001 | Kadash et al. |
| 6,241,747 B1 | 6/2001 | Ruff |
| 6,258,995 B1 | 7/2001 | Gilding et al. |
| 6,261,276 B1 | 7/2001 | Reitsma |
| 6,266,859 B1 | 7/2001 | Hernandez |
| 6,287,316 B1 | 9/2001 | Agarwal et al. |
| 6,345,623 B1 | 2/2002 | Heaton et al. |
| 6,368,305 B1 | 4/2002 | Dutton |
| 6,387,082 B1 | 5/2002 | Freeman |
| 6,458,109 B1 | 10/2002 | Henley et al. |
| 6,461,467 B2 | 10/2002 | Blatchford et al. |
| 6,467,432 B1 | 10/2002 | Lewis et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,800,074 B2 | 10/2004 | Henley et al. |
| 6,814,079 B2 | 11/2004 | Heaton et al. |
| 6,825,246 B1 | 11/2004 | Fattman |
| 6,855,135 B2 | 2/2005 | Lockwood et al. |
| 6,913,573 B1 | 7/2005 | Viscomi et al. |
| 6,979,324 B2 | 12/2005 | Bybordi et al. |
| 6,986,234 B2 | 1/2006 | Liedtke |
| 7,070,584 B2 | 7/2006 | Johnson et al. |
| 7,117,869 B2 | 10/2006 | Heaton et al. |
| 7,198,046 B1 | 4/2007 | Argenta et al. |
| 7,216,651 B2 | 5/2007 | Argenta et al. |
| 7,273,054 B2 | 9/2007 | Heaton et al. |
| 7,316,672 B1 | 1/2008 | Hunt et al. |
| 7,341,574 B2 | 3/2008 | Schreijag |
| 7,448,653 B2 | 11/2008 | Jensen et al. |
| 7,461,158 B2 | 12/2008 | Rider et al. |
| 7,485,112 B2 | 2/2009 | Karpowicz et al. |
| 7,520,872 B2 | 4/2009 | Biggie et al. |
| 7,569,745 B2 | 8/2009 | Sticklen et al. |
| 7,597,690 B2 | 10/2009 | Tanio et al. |
| D607,112 S | 12/2009 | Rogers et al. |
| D618,337 S | 6/2010 | Pratt et al. |
| 7,763,000 B2 | 7/2010 | Risk, Jr. et al. |
| 7,771,377 B2 | 8/2010 | Stapf et al. |
| 7,779,625 B2 | 8/2010 | Joshi et al. |
| D624,177 S | 9/2010 | Pratt et al. |
| 7,794,438 B2 | 9/2010 | Henley et al. |
| 7,837,673 B2 | 11/2010 | Vogel |
| 7,863,495 B2 | 1/2011 | Aali |
| 7,875,761 B2 | 1/2011 | Budig et al. |
| 7,880,050 B2 | 2/2011 | Robinson et al. |
| 7,926,856 B2 | 4/2011 | Smutney et al. |
| 7,928,279 B2 | 4/2011 | Rosenberg |
| 7,928,281 B2 | 4/2011 | Augustine |
| 7,942,866 B2 | 5/2011 | Radl et al. |
| 7,959,624 B2 | 6/2011 | Riesinger |
| 8,007,257 B2 | 8/2011 | Heaton et al. |
| 8,007,491 B2 | 8/2011 | Pinto et al. |
| 8,128,607 B2 | 3/2012 | Hu et al. |
| 8,148,595 B2 | 4/2012 | Robinson et al. |
| 8,162,908 B2 | 4/2012 | Hu et al. |
| 8,177,764 B2 | 5/2012 | Hu et al. |
| 8,287,507 B2 | 10/2012 | Heaton et al. |
| 8,308,705 B2 | 11/2012 | Lin et al. |
| 8,337,474 B2 | 12/2012 | Hu et al. |
| 8,361,043 B2 | 1/2013 | Hu et al. |
| 8,409,156 B2 | 4/2013 | Kazala, Jr. et al. |
| 8,409,157 B2 | 4/2013 | Haggstrom et al. |
| 8,535,283 B2 | 9/2013 | Heaton et al. |
| 8,641,692 B2 | 2/2014 | Tout et al. |
| 8,679,079 B2 | 3/2014 | Heaton et al. |
| 8,864,748 B2 | 10/2014 | Coulthard et al. |
| 2001/0031943 A1 | 10/2001 | Urie |
| 2001/0043943 A1 | 11/2001 | Coffey |
| 2002/0026133 A1 | 2/2002 | Augustine et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0150720 A1 | 10/2002 | Howard et al. |
| 2002/0173808 A1 | 11/2002 | Houser et al. |
| 2002/0183702 A1 | 12/2002 | Henley et al. |
| 2002/0198503 A1 | 12/2002 | Risk, Jr. et al. |
| 2003/0050594 A1 | 3/2003 | Zamierowski |
| 2003/0088201 A1 | 5/2003 | Darcey |
| 2003/0120194 A1 | 6/2003 | Stapf |
| 2003/0190339 A1 | 10/2003 | Skover et al. |
| 2004/0249353 A1 | 12/2004 | Risks, Jr. et al. |
| 2004/0261642 A1 | 12/2004 | Hess |
| 2005/0101940 A1 | 5/2005 | Radl et al. |
| 2005/0192544 A1 | 9/2005 | Wolbring et al. |
| 2005/0222527 A1 | 10/2005 | Miller et al. |
| 2005/0261642 A1* | 11/2005 | Weston ............... A61M 1/0088 604/313 |
| 2005/0267433 A1 | 12/2005 | Tanio et al. |
| 2006/0253090 A1 | 11/2006 | Bradley et al. |
| 2006/0282028 A1 | 12/2006 | Howard et al. |
| 2007/0027414 A1 | 2/2007 | Hoffman et al. |
| 2007/0066946 A1 | 3/2007 | Haggstrom et al. |
| 2007/0066948 A1 | 3/2007 | Erdman |
| 2007/0219512 A1 | 9/2007 | Heaton et al. |
| 2007/0219532 A1 | 9/2007 | Karpowicz et al. |
| 2007/0233022 A1 | 10/2007 | Henley et al. |
| 2007/0265586 A1* | 11/2007 | Joshi ................... A61M 1/0031 604/313 |
| 2008/0004559 A1 | 1/2008 | Riesinger |
| 2008/0009812 A1 | 1/2008 | Riesinger |
| 2008/0033330 A1* | 2/2008 | Moore ................ A61B 5/445 602/43 |
| 2008/0063615 A1 | 3/2008 | MacDonald et al. |
| 2008/0082059 A1 | 4/2008 | Fink et al. |
| 2008/0086214 A1 | 4/2008 | Hardin et al. |
| 2008/0108977 A1 | 5/2008 | Heaton et al. |
| 2008/0200906 A1 | 8/2008 | Sanders et al. |
| 2008/0234641 A1 | 9/2008 | Locke et al. |
| 2008/0294147 A1 | 11/2008 | Radl et al. |
| 2008/0306448 A1 | 12/2008 | Lee |
| 2008/0306456 A1 | 12/2008 | Riesinger |
| 2009/0012482 A1 | 1/2009 | Pinto et al. |
| 2009/0076467 A1 | 3/2009 | Pinto et al. |
| 2009/0187130 A1 | 7/2009 | Asmus et al. |
| 2009/0221977 A1 | 9/2009 | Blott et al. |
| 2009/0240218 A1 | 9/2009 | Braga et al. |
| 2009/0254066 A1 | 10/2009 | Heaton et al. |
| 2010/0030166 A1 | 2/2010 | Tout et al. |
| 2010/0036333 A1 | 2/2010 | Schenk, III et al. |
| 2010/0042021 A1 | 2/2010 | Hu et al. |
| 2010/0042059 A1 | 2/2010 | Pratt et al. |
| 2010/0100063 A1 | 4/2010 | Joshi et al. |
| 2010/0137775 A1 | 6/2010 | Hu et al. |
| 2010/0145289 A1 | 6/2010 | Lina et al. |
| 2010/0160879 A1 | 6/2010 | Weston |

(56) References Cited

U.S. PATENT DOCUMENTS

| | | |
|---|---|---|
| 2010/0160901 A1 | 6/2010 | Hu et al. |
| 2010/0168719 A1 | 7/2010 | Chen |
| 2010/0174250 A1 | 7/2010 | Hu et al. |
| 2010/0179493 A1 | 7/2010 | Heagle et al. |
| 2010/0198174 A1 | 8/2010 | Hu et al. |
| 2010/0228205 A1 | 9/2010 | Hu et al. |
| 2010/0262090 A1 | 10/2010 | Riesinger |
| 2010/0262094 A1 | 10/2010 | Walton et al. |
| 2010/0324510 A1 | 12/2010 | Andresen et al. |
| 2011/0106030 A1 | 5/2011 | Scholz |
| 2011/0130691 A1 | 6/2011 | Hu et al. |
| 2011/0137270 A1 | 6/2011 | Hu et al. |
| 2011/0313377 A1 | 12/2011 | Pinto et al. |
| 2012/0016325 A1 | 1/2012 | Pinto et al. |
| 2012/0078207 A1 | 3/2012 | Hu et al. |
| 2013/0006204 A1 | 1/2013 | Hu et al. |
| 2013/0090615 A1 | 4/2013 | Jaeb et al. |
| 2013/0144231 A1 | 6/2013 | Hu et al. |
| 2014/0100539 A1 | 4/2014 | Coulthard et al. |
| 2014/0200535 A1 | 7/2014 | Locke et al. |
| 2015/0018784 A1 | 1/2015 | Coulthard et al. |
| 2015/0094673 A1 | 4/2015 | Pratt et al. |
| 2015/0094674 A1 | 4/2015 | Pratt et al. |

FOREIGN PATENT DOCUMENTS

| | | |
|---|---|---|
| AU | 755496 B2 | 12/2002 |
| CA | 2005436 A1 | 6/1990 |
| CN | 1438904 A | 8/2003 |
| CN | 2851641 Y | 12/2006 |
| DE | 26 40 413 A1 | 3/1978 |
| DE | 43 06 478 A1 | 9/1994 |
| DE | 29 504 378 U1 | 9/1995 |
| DE | 19517699 A1 | 11/1996 |
| DE | 202004017052 U1 | 6/2005 |
| DE | 20 2005 019 670 U1 | 6/2006 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0360329 A1 | 3/1990 |
| EP | 1018967 A1 | 7/2000 |
| EP | 2098257 A1 | 9/2009 |
| FR | 1163907 A | 10/1958 |
| GB | 692578 A | 6/1953 |
| GB | 2 195 255 A | 4/1988 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 306 107 A | 4/1997 |
| GB | 2 329 127 A | 3/1999 |
| GB | 2 333 965 A | 8/1999 |
| GB | 2 431 351 A | 4/2007 |
| JP | 55-68370 A | 5/1980 |
| JP | 59-177055 A | 10/1984 |
| JP | 4-506760 A | 11/1992 |
| JP | 11-504833 A | 5/1999 |
| JP | 2003-284770 A | 10/2003 |
| JP | 2003-532504 A | 11/2003 |
| JP | 2007-534403 A | 11/2007 |
| JP | 4129536 B2 | 8/2008 |
| JP | 2010-506615 A | 3/2010 |
| SG | 71559 | 4/2002 |
| WO | 80/02182 A1 | 10/1980 |
| WO | WO-80/02182 A1 | 10/1980 |
| WO | 87/04626 A1 | 8/1987 |
| WO | 90/010424 A1 | 9/1990 |
| WO | 1991/000718 A1 | 1/1991 |
| WO | 93/009727 A1 | 5/1993 |
| WO | 94/020041 A1 | 9/1994 |
| WO | 96/05873 A1 | 2/1996 |
| WO | 1996/035401 A1 | 11/1996 |
| WO | 97/18007 A1 | 5/1997 |
| WO | 99/13793 A1 | 3/1999 |
| WO | 01/85248 A1 | 11/2001 |
| WO | 2001/085248 A1 | 11/2001 |
| WO | 2003/070135 A2 | 8/2003 |
| WO | 2004/037334 A1 | 5/2004 |
| WO | 2005/051461 A1 | 6/2005 |
| WO | 2005/105179 A1 | 11/2005 |
| WO | WO-2006/005939 A2 | 1/2006 |
| WO | 2006/048240 A1 | 5/2006 |
| WO | 2007030598 A2 | 3/2007 |
| WO | WO-2007/030601 A2 | 3/2007 |
| WO | WO-2007/067685 A2 | 6/2007 |
| WO | 2007/123451 A1 | 11/2007 |
| WO | 2008/048527 A2 | 4/2008 |
| WO | WO-2008/100446 A2 | 8/2008 |
| WO | WO-2008/112304 A1 | 9/2008 |
| WO | 2009/002260 A1 | 12/2008 |
| WO | WO-2009/089016 A1 | 7/2009 |
| WO | WO-2009/103031 A1 | 8/2009 |
| WO | WO-2010/068502 A1 | 6/2010 |
| WO | 2010/080907 A1 | 7/2010 |
| WO | WO-2010/102146 A1 | 9/2010 |
| WO | 2013/078214 A1 | 5/2013 |

OTHER PUBLICATIONS

Office Action received for Australian Patent Application No. 2009214439, dated May 9, 2013, 3 pages.

Office Action received for Chinese Patent Application No. 200980112984.X, dated Dec. 4, 2012, 13 pages (5 pages of English Translation and 8 pages of Official Copy).

Office Action received for Chinese Patent Application No. 200980112984.X, dated Aug. 16, 2013, 11 pages (4 pages of English Translation and 7 pages of Official Copy).

Office Action received for European Patent Application No. 09832371.0, dated Oct. 30, 2013, 5 pages.

Office Action received for Japanese Patent Application No. 2012-229673, dated Sep. 17, 2013, 5 pages (3 pages of English Translation and 2 pages of Official Copy).

Final Office Action received for U.S. Appl. No. 12/646,856, dated Nov. 4, 2013, 19 pages.

"Mask—Medical Definition and More from Merriam-Webster", available at <http://www.merriam-webstercom/medical/mask>, accessed on Aug. 25, 2012, 2 pages.

Non Final Office Action received for U.S. Appl. No. 12/626,426 dated Mar. 1, 2013, 9 pages.

Final Office Action received for U.S. Appl. No. 12/626,426 dated Aug. 31, 2012, 22 pages.

"3M Tegaderma Hydrocolloid Dressing", Sacral-6-¾"×6-⅜", 1 page.

"Adhesive Sacral Dressing", Smith & Nephew, 3 pages.

"EuroMed, Hydrocolloid Health Technologies", Product Catalog, 11 pages.

PolyMem QuadraFoam, Case Study, Huge Saral Pressure Ulcer in Four Months Using PolyMen Silver and PolyMem Wic Silver Dressings, Presented at 17th Conference of the European Wound Management Association, Poster #135, May 2-4, 2007. Glasgow, Scotland, 2 pages.

"PolyMem Quadrafoam", located at <http://www.verebrun.com>, 4 pages.

Office Action received for European Patent Application No. 09709714.1, dated Jan. 26, 2011, 4 pages.

Office Action received for European Patent Application No. 09709714.1, dated Mar. 20, 2013, 4 pages.

Extended European Search Report received for European Patent Application No. 09832371.0, dated Feb. 26, 2013, 8 pages.

Written Opinion received for PCT Patent Application No. PCT/US2008/003412, dated Jul. 28, 2008, 5 pages.

Written Opinion received for PCT Patent Application No. PCT/US2009/034158, dated May 29, 2009, 7 pages.

International Preliminary Report on Patentability received for PCT Patent Application No. PCT/US2009/034158, dated Aug. 17, 2010, 8 pages.

(56) References Cited

OTHER PUBLICATIONS

International Search Report and Written Opinion received for PCT Patent Application No. PCT/US2010/020368, dated Feb. 26, 2010, 7 pages.
International Preliminary Report on Patentability received for PCT Patent Application No. PCT/US2010/020368, dated Jul. 12, 2011, 6 pages.
International Preliminary Report on Patentability received for PCT Patent Application No. PCT/US2010/026269, dated Sep. 15, 2011, 9 pages.
Non Final Office Action received for U.S. Appl. No. 12/234,530, dated Nov. 16, 2010, 14 pages.
Notice of Allowance received for U.S. Appl. No. 13/245,735, dated Mar. 7, 2012, 7 pages.
Notice of Allowance received for U.S. Appl. No. 12/372,661, dated Apr. 9, 2012, 5 pages.
Non Final Office Action received for U.S. Appl. No. 12/717,838, dated Jun. 28, 2012, 14 pages.
Notice of Allowance received for U.S. Appl. No. 12/760,409, dated Jul. 17, 2012, 16 pages.
Final Office Action received for U.S. Appl. No. 12/646,856 dated Jul. 26, 2012, 18 pages.
Final Office Action received for U.S. Appl. No. 12/646,426, dated Dec. 12, 2012, 8 pages.
Non Final Office Action received for U.S. Appl. No. 12/683,987, dated Nov. 5, 2012, 21 pages.
Final Office Action received for U.S. Appl. No. 12/047,739, dated Nov. 7, 2012, 12 pages.
Fletcher, Jacqui, "World Wide Wounds, Dressings: Cutting and Application Guide", May 2007, available at: <http://www.worldwidewounds.com/2007/may/Fletcher/Fletcher-Dressings-Cutting-Guide.html>, 15 pages.
Notice of Allowance received for U.S. Appl. No. 12/683,987, dated Dec. 10, 2012, 7 pages.
Non Final Office Action received for U.S. Appl. No. 12/646,856 dated Feb. 26, 2013, 18 pages.
Final Office Action received for U.S. Appl. No. 12/717,838 dated Apr. 11, 2013, 15 pages.
Office Action received for Japanese Patent Application No. 2010-546944, dated Jun. 19, 2012, 4 pages.
"Atmosphere—Definition from the Merriam-Webster Online Dictionary", available at <http://www.merriam-webster.com/dictionary/atmosphere>, accessed on Nov. 20, 2009, 2 pages.
Wicks, Gills, "A Guide to the Treatment of Pressure Ulcers from Grade 1-Grade 4", Wound Essentials, vol. 2, 2007, pp. 106,108,110,112-113.
Gupta et al., "Differentiating Negative Pressure Wound Therapy Devices: An Illustrative Case Series", Wounds, vol. 19, No. 1, Jan. 2007, pp. 1-9.
Gokoo et al., Evaluation of Sacral Shaped Transparent Dressing Over Contoured and High Stress Areas, Health Care,1997, 4 pages.
Girolami, Susan, "Bio-Dome™ Technology: The Newest Approach to Negative Pressure Wound Therapy", 1 page.
Notice of Allowance received for U.S. Appl. No. 13/245,746, dated May 29, 2013, 10 pages.
Non Final Office Action received for U.S. Appl. No. 12/047,739, dated Jun. 21, 2013, 12 pages.
Non Final Office Action received for U.S. Appl. No. 13/221,734, dated Jul. 19, 2013, 9 pages.
Advisory Action received for U.S. Appl. No. 12/717,838, dated Jul. 5, 2013, 2 pages.
"McGraw-Hill Dictionary of Scientific and Technical Terms", 6th edition, 2003, 2 pages.
Computer Language Company Inc., "Computer Desktop Encyclopedia (CDE)", 1981, 2 pages.
Office Action received for Chinese Patent Application No. 200980112984.X, dated Mar. 19, 2014, 4 pages.
Extended European Search Report (Includes Supplementary European Search Report and Search Opinion) received for European Patent Application No. 08726845.4, dated Jun. 20, 2014, 7 pages.
Office Action Received for European Patent Application No. 09709714.1, dated Apr. 29, 2014, 8 pages.
Office Action received for Japanese Patent Application No. 2011-537745, dated Dec. 6, 2013, 7 pages.
Office Action received for Japanese Patent Application No. 2012-229674, dated Nov. 20, 2013, 5 pages.
Office Action received for Japanese Patent Application No. 2010-546944, dated Apr. 1, 2013, 5 pages.
Office Action Received for Japanese Patent Application No. 2010-546944, dated Mar. 3, 2014, 3 pages.
Office Action Received for Japanese Patent Application No. 2011-537745, dated Apr. 15, 2014, 4 pages.
Office Action Received for Japanese Patent Application No. 2012-229673, dated May 30, 2014, 4 pages.
Final Office Action received for U.S. Appl. No. 12/047,739, dated Feb. 13, 2014, 16 pages.
Final Office Action received for U.S. Appl. No. 12/626,426, dated Jan. 3, 2014, 11 pages.
Notice of Allowance received for U.S. Appl. No. 12/717,838, dated Jan. 8, 2014, 10 pages.
Non-Final Office Action received for U.S. Appl. No. 13/020,685, dated Feb. 14, 2014, 9 pages.
Final Office Action received for U.S. Appl. No. 13/221,734 dated Feb. 26, 2014, 13 pages.
Non-Final Office Action received for U.S. Appl. No. 13/221,734, dated Jun. 19, 2014, 11 pages.
Non-Final Office Action received for U.S. Appl. No. 13/752,206, dated Apr. 29, 2014, 14 pages.
Advisory Action received for U.S. Appl. No. 12/646,856, dated Jan. 29, 2014, 3 pages.
Office Action Received for Australian Patent Application No. 2009214439, dated Jul. 1, 2014, 4 pages.
Intention to grant received for European Patent Application No. 09832371.0, dated Jun. 2, 2014, 5 pages.
Non-Final Office Action Received for U.S. Appl. No. 13/077,857, dated Jul. 17, 2014, 12 pages.
Extended European Search Report (includes Supplementary European Search Report and Search Opinion) received for European Patent Application No. 14187150.9, dated Dec. 10, 2014, 6 pages.
Non Final Office Action received for U.S. Appl. No. 12/047,739, dated May 15, 2015, 15 pages.
Non-Final Office Action received for U.S. Appl. No. 12/626,426, dated Dec. 23, 2014, 14 pages.
Notice of Allowance received for U.S. Appl. No. 13/020,685, dated Oct. 15, 2014, 9 pages.
Non Final Office Action received for U.S. Appl. No. 13/077,857, dated Apr. 24, 2015, 9 pages.
Final Office Action received for U.S. Appl. No. 13/221,734, dated Apr. 9, 2015, 9 pages.
Notice of Allowance received for U.S. Appl. No. 13/615,173, dated Sep. 24, 2014, 7 pages.
Final Office Action received for U.S. Appl. No. 13/752,206, dated Oct. 31, 2014, 12 pages.
Non Final Office Action received for U.S. Appl. No. 13/752,206, dated Apr. 23, 2015, 6 pages.
Notice of Allowance received for U.S. Appl. No. 13/752,206, dated Oct. 7, 2015, 7 pages.
Notice of Acceptance received for Australian Patent Application No. 2009214439, dated Sep. 10, 2014, 2 pages.
Office Action received for Australian Patent Application No. 2009324913, dated Feb. 24, 2015, 4 pages.
Notice of Allowance received for Canadian Patent Application No. 2,715,645, dated Mar. 12, 2015, 1 page.
Notice of Allowance received for Japanese Patent Application No. 2011-537745, dated Dec. 10, 2014, 3 pages of Official Copy only. (See Communication under 37 CFR § 1.98(a) (3).
Notice of Allowance received for Japanese Patent Application No. 2012-229673, dated Dec. 16, 2014, 3 pages of Official Copy only. (See Communication under 37 CFR § 1.98(a) (3).
Office Action received for Japanese Patent Application No. 2012-229674, dated Nov. 27, 2014, 2 pages of Official Copy only. (See Communication under 37 CFR § 1.98(a) (3).

(56) References Cited

OTHER PUBLICATIONS

Anonymous. (Feb. 10, 2000). "Drain and Suture Line Care for Wounds," *The Cleveland Clinic Foundation*, located at <http://www.clevelandclinic.org/health/health-info/docs/2200/2205.asp?i . . . >, last visited Oct. 15, 2007, four pages.
Bagautdinov, N.A. (1986). "Variant of External Vacuum Aspiration in the Treatment of Purulent Diseases of Soft Tissues," in *Current Problems in Modern Clinical Surgery*, Volkov, V.Y. et al. eds., Cheboksary: Chuvashia State University, 14 pages. (includes English translation and translation certifications).
Chariker, M.E. et al. (Jun. 1989). "Effective Management of Incisional and Cutaneous Fistulae with Closed Suction Wound Drainage," *Contemporary Surgery* 34:59-63.
Davydov, Y.A. et al. (Sep. 1986). "Vacuum Therapy in the Treatment of Purulent Lactation Mastitis," *The Kremlin Papers: Perspectives in Wound Care* pp. 5-7.
Davydov, Y.A. et al. (Oct. 1988). "The Bacteriological and Cytological Assessment of Vacuum Therapy of Purulent Wounds," *The Kremlin Papers: Perspectives in Wound Care* pp. 11-14.
Davydov, Y.A. et al. (Feb. 1991). "Concepts for Clinical Biological Management of the Wound Process in the Treatment of Purulent Wounds Using Vacuum Therapy," *The Kremlin Papers: Perspectives in Wound Care* pp. 15-17.
Final Office Action dated Apr. 21, 2010, for U.S. Appl. No. 12/047,739, filed Mar. 13, 2008, 16 pages.
Final Office Action dated Apr. 22, 2010, for U.S. Appl. No. 12/234,530, filed Sep. 19, 2008, 16 pages.
Herrmann, L.G. et al. (1934). "The Conservative Treatment of Arteriosclerotic Peripheral Vascular Diseases: Passive Vascular Exercises (Pavaex Therapy)," *Ann. Surgery* pp. 750-760.
International Preliminary Report on Patentability dated Sep. 24, 2009, for PCT Application No. PCT/US2008/003412, filed Mar. 13, 2008, seven pages.
International Preliminary Report on Patentability dated Jun. 9, 2011, for PCT Application No. PCT/US2009/065959, filed Nov. 25, 2009, nine pages.
International Search Report dated Jul. 28, 2008, for PCT Application No. PCT/US08/03412, filed Mar. 13, 2008, three pages.
International Search Report dated May 29, 2009, for PCT Application No. PCT/US2009/034158, filed Feb. 13, 2009, two pages.
International Search Report dated Jan. 21, 2010, for PCT Application No. PCT/US09/65959, filed on Nov. 25, 2009, five pages.
International Search Report dated May 4, 2010, for PCT Application No. PCT/US2010/026269, filed on Mar. 4, 2010, four pages.
Kostiuchenok, B.M. et al. (Sep. 1986). "The Vacuum Effect in the Surgical Treatment of Purulent Wounds," *The Kremlin Papers: Perspectives in Wound Care* pp. 3-4.
Meyer, D.C. et al. (Jun. 2005). "Weight-Loaded Syringes as a Simple and Cheap Alternative to Pumps for Vacuum-Enhanced Wound Healing," *Plastic and Reconstructive Surgery* 115(7):2174-2176, located at <http://gateway.tx.ovid.com.laneproxy.stanford.edu/gw2/ovidweb.cgi>, last visited on Oct. 15, 2007.
Non-Final Office Action dated Oct. 29, 2009, for U.S. Appl. No. 12/234,530, filed Sep. 19, 2008, 14 pages.
Non-Final Office Action dated Nov. 27, 2009, for U.S. Appl. No. 12/047,739, filed Mar. 13, 2008, 18 pages.
Non-Final Office Action dated Oct. 12, 2011, for U.S. Appl. No. 12/626,426, filed Nov. 25, 2009, 14 pages.
Non-Final Office Action dated Nov. 2, 2011, for U.S. Appl. No. 12/646,856, filed Dec. 23, 2009, 15 pages.
Non-Final Office Action dated Nov. 18, 2011, for U.S. Appl. No. 13/245,735, filed Sep. 26, 2011, 13 pages.
Non-Final Office Action dated Dec. 23, 2011, for U.S. Appl. No. 13/245,746, filed Sep. 26, 2011, 10 pages.
Non-Final Office Action dated Feb. 13, 2012, for U.S. Appl. No. 12/047,739, filed Mar. 13, 2008, 11 pages.
Notice of Allowance dated Jun. 24, 2011, for U.S. Appl. No. 12/234,530, filed Sep. 19, 2008, 11 pages.
Notice of Allowance dated Dec. 22, 2011, for U.S. Appl. No. 12/760,406, filed Apr. 14, 2010, eight pages.
Pre-Interview First Office Action dated Dec. 15, 2011, for U.S. Appl. No. 12/372,661, filed Feb. 17, 2009, three pages.
Svedman, P. (Sep. 3, 1983). "Irrigation Treatment of Leg Ulcers," *The Lancet* pp. 532-534.
Svedman, P. et al. (Aug. 1986). "A Dressing System Providing Fluid Supply and Suction Drainage Used for Continuous or Intermittent Irrigation," *Annals of Plastic Surgery* 17(2):125-133.
Ubbink, D.T. et al. (2009). "Topical Negative Pressure for Treating Chronic Wounds," *The Cochrane Collaboration* 3:1-32.
Urschel, J.D. et al. (1988). "The Effect of Mechanical Stress on Soft and Hard Tissue Repair; a Review," *British Journal of Plastic Surgery* 41:182-186.
Usupov, Y.N. et al. (Apr. 1987). "Active Wound Drainage," *The Kremlin Papers: Perspectives in Wound Care* pp. 8-10.
Written Opinion dated May 4, 2010, for PCT Application No. PCT/US2010/026269, filed on Mar. 4, 2010, seven pages.
Written Opinion of the International Searching Authority dated Jan. 21, 2010, for PCT Application No. PCT/US09/65959, filed on Nov. 25, 2009, seven pages.
Japanese Second Office Action, Notice of Rejection, dated May 26, 2016 corresponding to JP Application No. 2015-001376. (with English Translation).
Partial ISR for corresponding PCT/US2017/018129, mailed May 15, 2017.
Louis C. Argenta, MD and Michael J. Morykwas, PhD; Vacuum-Assisted Closure: A New Method for Wound Control and and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

(56) References Cited

OTHER PUBLICATIONS

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

PRESSURE INDICATOR

CROSS-REFERENCE TO RELATED APPLICATIONS

This is a continuation of U.S. application Ser. No. 12/626,426, filed on Nov. 25, 2009, which claims benefit under 35 U.S.C. § 119(e) to U.S. Provisional Ser. No. 61/117,921, filed on Nov. 25, 2008, and to U.S. Provisional Ser. No. 61/117,920, filed on Nov. 25, 2008, which are hereby incorporated by reference in their entirety.

BACKGROUND

The use of sub-atmospheric pressure to treat wounds can be traced back to ancient civilizations. For example, the ancient Chinese used "Cupping," a technique that creates reduced pressure environment by flaming then applying to the skin a glass chamber to draw out bad humors from the body. Modern research has revealed that applying reduced pressure to damaged tissue may have several beneficial effects: 1) a reduced pressure level may lead to retraction of the damaged tissue edges and thus may reduce the defect size and may expedite healing by facilitating wound contraction; 2) the reduced pressure may provide mechanical stimulation to the damaged tissue which may release growth factors at the wound bed to promote healing; 3) the reduced pressure may create suction in the damaged tissue cavity which may remove necrotic tissue from the damaged tissue cavity and may reduce bacterial load; 4) the application of reduced pressure may increase blood flow to the damaged tissue which may expedite healing; 5) reduced pressure may remove granulation inhibiting metalloproteinase enzymes which may enhance tissue remodeling and healing.

SUMMARY OF THE INVENTION

Disclosed herein is a device which is intended to deliver and maintain reduced pressure to body surfaces for application of reduced pressure wound therapy (RPWT) also known as negative pressure wound therapy (NPWT). During application of this type of therapy, a substantially airtight seal is formed around a section of tissue to be treated. This seal is formed by a dressing which provides fluid communication from a section of tissue to a reduced pressure source. The dressing system may be configured to enhance usability and functionality of this dressing, or to otherwise be configured with more optimal sealing characteristics, improved peri-wound skin protection, and with easier application than traditional RPWT dressing systems. In some examples, the dressing may comprise an adhesive layer comprising a flowable adhesive having a sufficient volume or thickness to fill micro-cracks and fissures in the skin surface to reduce dressing leakage rates, as well as gaps in the dressing that may form when the dressing buckles or wrinkles. The adhesive may also have moisture absorbent characteristics to reduce tissue maceration.

The dressing system may be configured with any of a variety of other features. First, the system may be configured to allow full rotation of the fluid communication conduit to the reduced pressure source along the axis substantially normal to the dressing. Second, the system may be configured to include a one-way valve to prevent backflow of any drainage fluids. Third, the system may be configured with transparent windows covered by opaque flaps to allow inspection through the dressing. Fourth, the system may be configured to include an indicator which visually makes clear whether reduced pressure is being applied or not. Fifth, the system is configured to minimize the profile of the dressing system.

In one embodiment, a reduced pressure treatment system is provided, comprising a cover structure comprising an outer edge, an upper surface, a lower surface, and at least one opening, a flowable adhesive layer attached to the lower surface of the cover structure, wherein the flowable adhesive layer has a thickness of at least about 0.2 mm, and a non-electrically powered, self-generating vacuum source. The system may further comprise tubing configured to attach to the vacuum source. The vacuum source may be integrally formed with the cover structure. The cover structure may further comprise a port member attached to at least the upper surface of the cover structure. The flowable adhesive layer may comprise a moisture absorbent flowable adhesive layer. In some variations, the adhesive layer may have a water absorbency rate of at least 900 g/m2/day, 1000 g/m2/day, 1100 g/m2/day or 1200 g/m2/day or more. In some other examples, the flowable adhesive layer may have a thickness of at least about 0.3 mm, about 0.5 mm, about 0.7 mm, about 1 mm or at least about 1.5 mm. In some instances, the flowable adhesive layer may have a viscosity in the range of about 20,000 to about 50,000 centipoise, or about 10,000 to about 100,000 centipoise.

In another embodiment, a reduced pressure treatment system is provided, comprising a cover structure comprising an outer edge, an upper surface a lower surface, and at least one opening, a port member attached to the upper surface of the cover structure and comprising at least one port lumen in communication with the at least one opening of the cover structure, and a hydrocolloid layer attached to the lower surface of the cover structure, wherein the hydrocolloid layer has a thickness of at least about 0.2 mm. The hydrocolloid layer may comprise a reduced thickness region about the outer edge of the cover structure. In some examples, the reduced thickness region may comprise an embossed or compressed region, and/or may comprise an increased density relative to an interior region of the hydrocolloid layer. In some examples, the system may further comprise visual grid markings on the cover structure. In further examples, the port member may further comprise a base and a body configured to rotate with respect to the base. The base of the port member may be adhered to the upper surface of the cover structure. The system may further comprise tubing, the tubing comprising an outer wall, a proximal end, a distal end, at least one lumen therebetween, a longitudinal lumen axis, a first dimension transverse to the longitudinal lumen axis and a second dimension transverse to the first dimension and the longitudinal lumen axis. The tubing may also be configured to attach to the port member, or may be integrally formed with the port member. In some variations, the first dimension of the tubing may be greater in size than the second dimension, and in some variations, may be at least twice the size of than the second dimension, three times the size or four times the size or more. The tubing may also comprise a plurality of lumens in a generally planar configuration. In some examples, the at least one port lumen has a non-circular cross-sectional configuration, and may also comprise at least one lumen projection, which may be a plurality of longitudinal ridges. The tubing may also further comprise at least one side passageway providing communication between at least one lumen of the tubing and the outer wall. The system may also further comprise an elastomeric structure sealed to the outer surface of the tubing and covering the at least one side passageway, wherein the elastomeric structure may be a sleeve structure. In other examples, the elastomeric structure may be configured with an interior surface that is spaced a first distance from the outer wall of the tubing when the interior surface is exposed to atmospheric pressure and a second distance less than the first distance when the interior surface is exposed to a reduced pressure. In still other examples, the port member may comprise an elastomeric material. Sometimes, at least a portion of the elastomeric material may be configured to deform into the at least one port lumen when an internal pressure level within the at least one port lumen is at least about −50 mm Hg, about −75 mm Hg, about −100 mm Hg, or −125 mm Hg lower than atmospheric pressure. The cover structure may further comprise a reinforcement structure, which may be integrally formed with the cover structure. In some examples, the reinforcement structure comprises a first ridge structure on the upper surface of the cover structure and surrounding the port member. The system may also further comprise a second ridge structure surrounding the first ridge structure. The first ridge structure may be a segmented ridge structure. In some examples, the reinforcement structure may be embedded within cover structure.

The cover structure may also comprise a cover material and the reinforcement structure comprises a reinforcement material with an increased durometer than the cover material. The reinforcement structure may comprise a grid reinforcement structure, or a radial spoke structure. In some variations, the system may further comprise a release layer releasably adhered to at least a portion of the hydrocolloid layer. In some specific variations, the release layer may be releasably adhered to a central portion of the hydrocolloid layer, and the system may further comprise at least one or two handle layer(s) releasably adhered to at least a peripheral portion of the hydrocolloid layer and located between the hydrocolloid layer and the release layer. The system may also further comprise an adhesive carrier structure detachably attached to the upper surface of the cover structure. The adhesive carrier structure may comprise a first carrier layer and a second carrier layer and a non-linear interface therebetween. The adhesive carrier may also comprise a central opening surrounding the port member. The central opening may be spaced apart from the port member, and in some variations, may be spaced at least 1 cm from the port member. In some examples, the hydrocolloid layer may have a greater probe tack force about the outer edge of the cover structure than about an interior region of the cover structure. The hydrocolloid layer may also have a greater release force about the outer edge of the cover structure than about an interior region of the cover structure. In some instances, the maximum perpendicular dimension of the port member to the cover structure may be less than the maximum transverse dimension of the port member that is transverse to the maximum perpendicular dimension, or may be less than the maximum transverse dimension of the port member that is transverse to the maximum perpendicular dimension. The tubing may also further comprise a one-way check valve.

In another embodiment, a method for performing reduced pressure treatment of a skin location is provided, comprising applying a dressing to a skin location, applying a mask to the skin location, the mask comprising an inner edge and an outer edge, applying a liquid sealant to the dressing and the skin location, and removing the mask from the skin location. The method may also further comprise selecting the mask to space the inner edge of the mask from the edge of the skin location. It may also further comprise placing a contact material onto the skin location, wherein the skin location is an open wound, placing a mesh material onto the liquid sealant after applying the liquid sealant to the dressing, placing the mesh material onto the liquid sealant after removing the mask from the skin location, or placing a mesh material onto the dressing before applying the liquid sealant.

DETAILED DESCRIPTION

Figure 1:
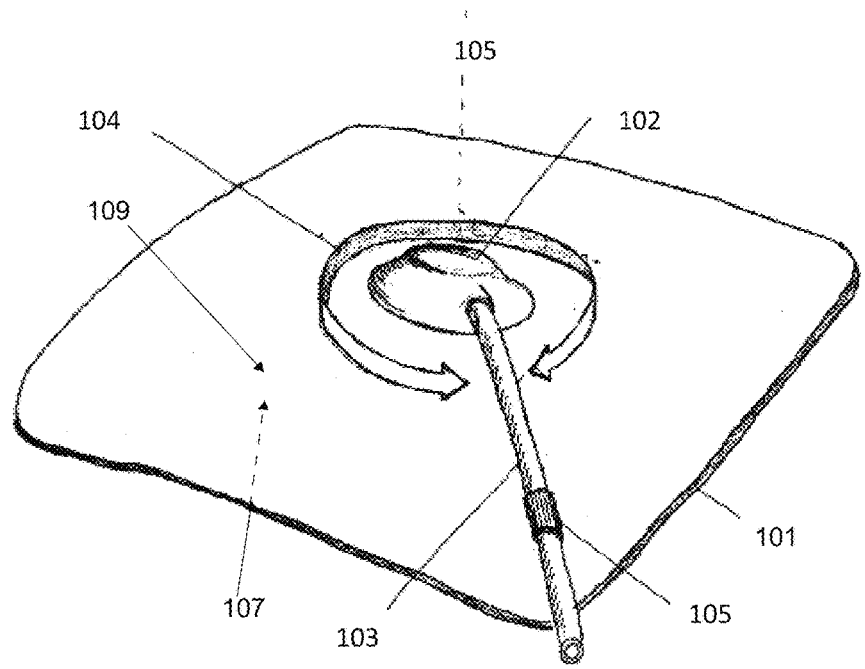
FIG. 1 depicts an example of a dressing configured for use with a vacuum source.

Application of reduced pressure to body sites has been shown to be therapeutically beneficial in several applications. One such area is the application of reduced pressure to damaged tissue such as chronic wounds in order to accelerate or promote healing. Regardless of the specific application area, application of reduced pressure requires formation of a substantially airtight seal.

In reduced pressure wound therapy (RPWT), a cover structure or dressing comprising an occlusive cover sheet with an adhesive layer is applied over the wound, which may be filled with a contact material such as gauze, foam or other porous materials, to provide cushioning and distribute the reduced pressure throughout the wound bed. The adhesive sheet may serve as a dressing and create a substantially airtight enclosure which encompasses the wound. This enclosure is in fluid communication with a reduced pressure source. The reduced pressure source may comprise an electric vacuum pump, in-wall suction, or a non-electrically powered suction device. The fluid communication between the vacuum source and the occlusive sheet is provided by a conduit which communicates with an opening in the occlusive sheet, or which passes through the dressing.

One of the major challenges in delivering RPWT is the application of the dressing and maintenance of a robust seal during treatment. Current techniques utilize thin polyurethane adhesive films that can easily wrinkle and fold onto themselves. These films frequently fail to remain airtight for a number of reasons, including mechanical deformation caused by patient movement and by the reduced pressure itself. The nature of the films, related to their mechanical characteristics and adhesive properties, make application difficult and time consuming. In addition, traditional dressings can be traumatic on removal to the delicate peri-wound skin and are not configured to treat smaller satellite wound lesions in the immediate peri-wound region of the main RPWT treated wound. Furthermore, there are locations with particular geometries that make application of a pre-fabricated dressing difficult and sometimes impractical, such as the bottom of toes.

For example, during the course of operation, reduced pressure applied to the dressing can lead to buckling of the dressing layer as it is drawn down over the contours to which it is adhered. For example a suction element attached to a dressing pulls on the surrounding dressing with application of reduced pressure and the contractile forces placed on the dressing can cause the dressing to buckle creating channels that radiate outward from the suction element attachment area. If these channels breach the dressing border, a leak path can form and compromise the desired seal. Dressing application can also lead to formation of wrinkles during handling and accommodation of anatomic curvatures. Healthcare practitioners frequently attempt to smooth out these wrinkles, but the properties of commonly used thin film dressing adhesives do not allow for sufficient filling of channels to close off leak paths that form and can be cumbersome to use. Therefore a need exists for an improved device and method of creating an airtight seal the wound site to which RPWT is to be applied.

In other general examples in wound care, transdermal drug delivery, and signal monitoring (i.e. EKGs), among other areas, the effective application of a dressing-type device or adhesive material to a body site may be complicated by the very aspects that lead to a high performance dressing once it is applied. Namely, pliable materials allow for a high degree of conformability to various body curvatures. Similarly, dressings that permit a fair amount of stretch accommodate natural body movement and flexion/extension motions. In combination with an appropriately adherent adhesive, these dressings can successfully stay on the body site for desired durations even under significant variations in external environmental conditions. Certain transdermal drug delivery patches, such as that by the ethinyl estradiol and norelgestromin transdermal patch sold under the trademark ORTHO EVRA®, are indicated to stay on for seven day durations while allowing normal daily activities as well as exercise including swimming. Successful application of these dressing systems can be confounded by the pliability that allows dressings to wrinkle and fold, particularly when the adhesive surfaces are exposed. Adhesive surfaces can often be difficult to separate once attached. Furthermore, highly stretchable materials may further exacerbate the situation because efforts to pull and separate material folds often leads to stretching of the dressing itself instead of the desired separation of self-adhered regions of the dressing. The quality of the adhesive can make it difficult to apply the desired surface to the body site as one's fingers may become stuck to the dressing surface.

On the other hand, while the adhesive strength of the dressing may be strong enough to prevent wrinkling or air channel leaks with movement, if the bond to the underlying skin is too strong, this can result in damage to the underlying skin upon dressing removal. This is especially true for patients with highly friable peri-wound skin which is common in many wound disorders such as venous stasis ulcers, traumatic wounds, diabetic ulcers, and pressure ulcers. Thus there exists a need to develop a RPWT dressing that optimizes adhesion for prevention of air leaks, but minimizes trauma from dressing removal to the underlying skin.

In some embodiments, the adhesive dressing material possesses improved crevice and leak channel filling and sealing properties as well as properties that protect and promote wound healing in the region around the treated wound. The dressing itself may have one or more specific properties that improve its ability to hold and maintain a seal and protect the peri-wound skin. Among these properties are (1) increased thickness of the dressing to facilitate placement and resist wrinkling that may lead to dressing wrinkling and seal leaks, (2) adhesion gradients on the undersurface of the dressing that allow for maximum sealing while maintaining minimum trauma to the peri-wound skin during removal, (3) adhesion strength characteristics that decrease over time to allow for strong sealing characteristics between dressing changes and easier and less traumatic removal of the dressing at the time period of dressing change, (4) a dual seal system with a thicker primary dressing and thinner peripheral dressing and backing system for simplified application, (5) a breathable dressing that prevents maceration of the underlying skin, (6) an absorptive dressing that prevents maceration of the underlying skin and promotes a moist wound healing environment for skin wounds around the central wound treated with RPWT, (7) support structures and thickness design elements that optimize rigidity and wrinkle protection while allowing for dressing conformation to a wound site, (8) a dressing configured such that upon activation the dressing flows and deforms to the body surface/skin contours to fill in potential leak channels, (9) a formulation such that the dressing can deform plastically such that stretching the dressing leads to a permanent deformation in the dressing enabling contouring of complex anatomical protrusions and intrusions with minimal elastic energy stored in the dressing layer, (10) a dressing system further configured to have sufficient rigidity to maintain its shape during application while remaining flexible enough to conform once applied to desired body topographies.

In some further examples, the dressing may be configured such that on activation the dressing flows and deforms to the body surface/skin contours to fill in potential leak channels. The adhesive layer of the dressing may comprise a semi-solid or flowable adhesive material. Some examples of such adhesives include but are not limited to hydrocolloid or hydrogel materials, silicone, pressure sensitive adhesives, and the like. In some specific embodiments, the adhesive material may be selected to have a glass transition temperature (Tg) that is at or near body core temperature (about 98.6° F.), room, temperature (anywhere from about 60° F. to about 90° F.) or body surface temperature (anywhere from about 70° F. to about 98° F., for example). In some variations, the Tg may be in the range of about ±1° F., about ±2° F., ±3° F., about ±4° F., about ±5° F., about ±6° F., about ±7° F., about ±8° F., about ±9° F., about ±10° F., about ±15° F., or about ±20° F. within body core temperature or a surface temperature about 60° F., about 65° F., about 70° F., about 75° F., about 80° F., about 85° F., about 90° F. or about 95° F. The adhesive dressing in one embodiment is also formulated to possess mechanical properties that allow it to flow and deform to fill paths or channels that may form during application and subsequent therapeutic use on a patient. This adhesive material may comprise a thicker acrylic adhesive, a hydrocolloid, a hydrogel or other such adhesive material without limitation. In some examples, the adhesive material may have a viscosity in the range of about 5,000 centipoise (cP) to about 500,000 cP, sometimes about 10,000 cP to about 100,000 cP, or other times about 20,000 cP to about 50,000 cP. In other examples, the adhesive material when subjected to low-frequency mechanical input (about <1 Hz) is selected to exhibit deformation properties and wear performance that may be characterized by a loss angle (tan δ) which equals the ratio of the loss modulus (viscous component) to the storage modulus (elastic component) of the tested material may be in the range of about 0.5 to about 2, sometimes about 0.5 to about 1, and other times about 0.5 to about 0.7.

In one configuration of the device the dressing is made of a hydrocolloid dressing that has some or all of the properties mentioned above, and/or one or more breathability, moisture absorbent abilities, skin protective properties, and wound healing characteristics. This dressing may also provide for a moist wound healing environment and is an appropriate dressing for satellite wound lesions. In one embodiment, the adhesive dressing may be formulated such that it flows on application of body heat and/or pressure to the dressing surface to eliminate potential leak channels that may form during application. In other embodiments, the application of light energy may also initiate a softening phenomenon to allow the adhesive to flow more readily and fill gaps.

In some embodiments of the sealant system, the film backing on which the adhesive layer resides is formulated to have desirable mechanical properties including elastic modulus and maximum elongation and stretch such that it is more compliant than the body site tissue it is adhered to in order to mitigate peeling and delamination of the dressing from the body surface. Having mechanical properties of the backing and adhesive layer tuned to be less stiff than that of the skin also leads to improved user comfort as the dressing material will not restrict movement. It is recognized that skin covering different areas of the body may have different mechanical properties, and the dressing's elasticity would be such that it would be able to accommodate the maximum possible stretch without applying excessive mechanical force on the underlying skin during normal distension. The dressing would also be flexible enough to conform to different geometries on the surface of the body. Some embodiments may be pre-shaped to provide optimal seal around irregular geometries such as around the toes or the sacral area.

In some embodiments, the dressing may be formulated to deform plastically such that stretching the dressing leads to a permanent deformation in the dressing enabling contouring of complex anatomical protrusions and intrusions with minimal elastic energy stored in the dressing layer. This stored elastic energy may tend to cause delamination of the dressing; so, its reduction may lead to better adherence of the dressing. This type of deformational plasticity might be highly useful in tailoring the dressing to regions like the foot or sacrum.

While some of the dressing application hurdles have been dealt with by others, in many cases, application of dressings is desired on different body sites. In some instances it is possible to make specific dressings for particular body sites to accommodate specific anatomy. However, even then, these dressings may not accommodate all anatomic variability and sometimes it is not practical to produce a dressing that will work for each possible anatomic location. Healthcare practitioners routinely find that certain dressings as received may not fit the needs of the patient and therefore proceed to cut or shape the dressing to fit the specific contours and body site requirements of the patient. This need for customization becomes particularly apparent with large dressings or body surface features with high curvature where folds and wrinkles can make good adhesion difficult. For transdermal drug delivery, proper adhesion dictates proper therapeutic drug dosing. In the case of signal monitoring, proper surface contact is critical. For RPWT, the quality of the seal around a wound site may be beneficial for maintenance of the reduced pressure, and leak paths can compromise therapeutic efficacy. The sealing properties of this dressing may be especially beneficial for RPWT devices that do not use a continuous electric pump or similar reduced pressure generation system, or otherwise have a limited suction capacity, as the tolerances for significant leaks is much lower than traditional RPWT devices. In many dressing systems, the dressing structures, such as release liners or handling flaps that permit easier application lose their functionality if the dressing must be shaped to fit a certain contour. Disclosed herein is a sealant system and method that mitigates formation of leak paths during and after application of said dressing by reducing folding of the dressing and adhesion of the dressing to itself or user while allowing simple dressing application to fit the needs of the individual after being cut to shape while possessing characteristics that permit the dressing adhesive to subsequently fill and close off channels that may form during or after the dressing application.

In addition, many wounds that may be treated by RPWT may have surrounding satellite wounds that are smaller and distinct from the central wound treated with RPWT. For example, patients with venous stasis ulcers often present with clusters of open skin areas. In addition, some wounds heal by skin bridging from epidermal migration across the wound. When this occurs, smaller proximal wounds can develop that are more near healing than other regions of the original wound. These types of satellite wounds may be too small to treat with RPWT, but may lie within the boundaries of where the dressing must cover to create a seal. Furthermore, many wounds are surrounded by highly friable and delicate skin that can be injured during frequent adhesive dressing removal. Traditional RPWT dressings do not address the needs of this peri-wound skin and satellite lesions, and there exists a need to develop a dressing that is both gentler to the peri-wound skin and may treat these satellite lesions with an appropriate dressing that promotes wound healing.

Furthermore, there are wounds that are located in regions of the body that using any type of pre-fabricated film would be difficult to apply. These regions might include wounds on the toes or fingers. Thus, there needs to be a dressing that can provide adequate sealing in these regions that can be tailored to the specific geometries of these locations.

The passage through the dressing is often times facilitated by a port feature on the top surface of the dressing. In the prior art, this port feature is fixed relative to dressing, which fixes the directional orientation of the fluid communication conduit once the dressing is adhered. In many applications, it may be advantageous to re-orient the fluid communication conduit direction after application of the dressing, since the user needs to account for the position and direction of the fluid communication conduit prior to and during application of the dressing. There exists a need for a port which allows re-orientation of the fluid communication conduit after application of the dressing without disrupting the dressing.

Wound drainage (e.g. exudates) is often times evacuated from the wound towards the reduced pressure source during the course of treatment of RPWT. If reduced pressure is interrupted or terminated, this drainage potentially may flow back into the wound, especially if the interrupted or terminated reduced pressure source is located at a higher elevation than the wound. Wound drainage may be contaminated with infectious microbes or compounds which are deleterious towards wound healing. Therefore, there exists a need to prevent wound drainage from flowing back to the wound in case of terminated or interrupted reduced pressure.

Use of a substantially opaque or aesthetically appealing dressing for RPWT may be advantageous, since it hides the wound and wound contact material from sight and may increase the psychological comfort of the patient and others. In some instances, it may also be advantageous to use a substantially transparent dressing, since clinicians may wish to inspect the wound, wound contact material or peri-wound skin without removing the dressing. Disclosed herein is a dressing which shields the wound from view normally, but also allows inspection under the dressing.

RPWT traditionally requires maintenance of reduced pressure at the wound bed for extended periods of time. It may be advantageous to have an indicator to show whether reduced pressure is present in the system or has been compromised, for example by a leak in the dressing. This may be particularly beneficial with closed system vacuum sources. Pressure indicators may include instrumentation such as dial indicators and pressure transducers. Often times, these may be large, bulky, require electricity or are expensive. Furthermore, often times, these indicators are located at the reduced pressure source and do not provide indication of the pressure at the site of the wound bed where its pressure information may be more useful. In case of disruption or clogging of the fluid communication conduit between the reduced pressure source and the dressing, these indicators may not detect that reduced pressure may be lost at the wound site but still present at the reduced pressure supply. There exists a need for a simple, inexpensive indicator to inform clinicians or patients whether reduced pressure is present at the wound or not.

Some of the wounds being treated with RPWT may be present due to tissue ischemia from pressure applied to a body site, e.g. decubitus wounds or pressure sores. To prevent or otherwise reduce the risk of continued degradation of the wound region and surrounding tissue, a low profile reduced pressure conduit that reduces concentration of force on the wound or surrounding tissue may be beneficial for proper therapeutic delivery of reduced pressure and for better wound healing. Current RPWT conduits often contain elements that can create additional pressure points over a wound if a load were to be applied onto the port component of the conduit. Disclosed herein is a negative pressure conduit that is low profile as to reduce the development of pressure points on the wound or surrounding tissues.

Disclosed herein are some embodiments of a device which enhance the functionality and/or usability of delivery of reduced pressure to body surfaces. One embodiment comprises a dressing, a fluid communication conduit and a port which allows passage of the fluid communication conduit from one side of the dressing to the other. The dressing may comprise at least one adhesive side which in practice may be adhered to a body surface to create a substantially airtight seal. The dressing and dressing adhesive may comprised polyurethane, hydrocolloid, hydrogel, silicone, acrylic, any other material or any combination thereof known in the art.

In some embodiments, the port is configured to allow at least some freedom of rotation around the axis substantially parallel to the plane of the dressing. In some embodiments, the freedom of rotation is provided by an o-ring seal and flange and groove system. In some embodiments, the port body comprises a substantially compliant elastomeric material bonded to substantially rigid elements which interact with substantially rigid elements on the dressing which together provide for substantially airtight seal of the rotational elements of the port. The port member may further comprise a connector configured to facilitate coupling to a fluid communication conduit that is then attached to the vacuum source. In other embodiments, at least a portion of the conduit may be integrally formed with the port member.

In some embodiments, the fluid communication conduit and/or port member passes through or transects the dressing and connects a sealed enclosure formed by the dressing with a reduced pressure source. In some embodiments, the fluid communication conduit comprises the port and tubing. In some embodiments, the tubing comprises a single lumen, while in other embodiments, the tubing may comprise multiple lumens.

In some embodiments, a one way flow mechanism may be interposed along the length of the fluid communication pathway between the dressing and the vacuum source. In some mechanisms, the one way flow mechanism is located in or integrated into the body of the port member, while in some embodiments, the one way flow mechanism may be integrated into the dressing or port-dressing interface. In still other embodiments, the one way flow mechanism may be located in or integrated into the tubing. In some embodiments, the one way flow mechanism may prevent or reduce the degree or risk of backflow of wound drainage collected by the reduced pressure source back to the wound. In some embodiments, the one way flow mechanism may be a one way valve, such as a duckbill valve, a slit valve, a spring valve, an umbrella valve or any other suitable one way valve known in the art. In some embodiments, a plurality of one way flow mechanisms may be interspersed throughout the fluid communication conduit. In further embodiments, the one way flow mechanisms may have non-uniform opening or cracking pressures to account for fluid pressure differentials from pressure head or flow rate.

In some embodiments of the device, the load concentration of the reduced pressure conduit and/or port member may be reduced during load bearing situations by reducing the height of the port and increasing its width. Reduction of load concentrations or pressure points may be further provided by the use of softer materials such as silicones or other materials known in the art to be able to deform under load. These materials may further be configured to possess similar mechanical properties as the skin such as durometer and elastic modulus. In some embodiments, the conduit in the port between the wound site and the tubing or reduced pressure source is reinforced with supports that prevent collapse of the conduit. In some embodiments, these supports are further configured to distribute loads applied to the device surface to reduce pressure concentrations. In some configurations of the device, the total cross-sectional surface area may be maintained relative to a round tube, but the height of the tubing (and thus nozzle) may be reduced by making the diameter wider and flatter to distribute loads more evenly. In addition, in certain configurations a multi-lumen conduit may be used to further reduce the external diameter and lower the profile of the nozzle and tubing.

In further configurations, the reduced pressure conduit may be integrated and potentially molded directly into the dressing material. In further embodiments, the reduced pressure conduit may be position through one or more openings or fenestrations of the dressing. In a further embodiment, the fenestration provides an insertion opening for an attachment port to connect a source of reduced pressure, or to connect an extension tube located on the outer surface of the dressing. In one embodiment, the reduced pressure conduit comprises a plurality of such fenestrations.

In one embodiment, the reduced pressure conduit or tubing comprises a hollow tubular structure which flares into and joins with the dressing material, enabling fluid communication between the volume beneath the bottom surface of the dressing and interior of the tubular structure. In one embodiment, the reduced pressure conduit is a resilient conduit embedded within the dressing with terminals connecting the bottom surface of the dressing and an attachment port on a side edge of the dressing. In one embodiment, the reduced pressure conduit is a series of such conduits.

In some embodiments, the reduced pressure conduit comprises a mechanism which allows quick attachment and detachment of the tube or reduced pressure source in an airtight manner.

In one configuration of the dressing, the dressing is integrated directly with the reduced pressure source and wound enclosure, e.g. a vacuum source attached directly to a port without an extension tube, and may also comprise further attachment of other portions of the vacuum source directly to the dressing to resist swinging or other motions of the vacuum source relative to the dressing. This eliminates may also reduce the need to puncture a hole and attach the vacuum source to the dressing, as required in some dressings, thereby mitigating application complexity, enabling successful application by non-healthcare professionals and eliminating another potential source of air leak. In this configuration, the vacuum source does not employ tubing, but directly integrates into the dressing.

In some embodiments of the disclosed invention, the fluid communication conduit and/or the port member comprises a reduced pressure indicator. In some embodiments, the reduced pressure indicator is located in or along the conduit tubing. In some embodiments, the reduced pressure indicator is located within the port. In some embodiments, the reduced pressure indicator is integrated into the body of the port. In some embodiments, the reduced pressure indicator is comprised of a compliant material which visibly deforms when a pressure gradient is applied across it. In some embodiments, the pressure gradient leads a color change to indicate that the proper level of pressure application is achieved. For example, a sufficiently translucent or transparent blue element in proximity to a yellow material with the application of reduced pressure can effect a color change and appear green to indicate application or non-application of reduced pressure.

Various examples of the above embodiments are provided in greater detail below.

FIG. 1 depicts one embodiment of a reduced pressure treatment system 100, comprising a cover structure or dressing 101 that may be attached to a vacuum source (not shown). The dressing 101 may comprise a flexible, adhesive sheet which may be placed over a body surface. Dressing 101 may further comprise release liners, carrier films or other features known in the art to facilitate application of the system 100 to a treatment site. Examples of the release liners and carrier films are provided in greater detail below. The dressing may comprise any of a variety of suitable sheet materials, including but not limited to polyurethane, silicone, vinyl, polyvinyl chloride, polyisoprene, latex, rubber, thermoplastic elastomers, hydrogels, hydrocolloids, and the like. In some examples, the stiffness of the sheet material may be in the range of about 59 N/m to about 138 N/m for a 25.4 mm wide specimen, sometimes about 19 N/m to about 59 N/m, and other times about 3 N/m to about 19 N/m. The sheet material may be optically transparent or translucent, or may be opaque. The sheet material may have a uniform or non-uniform thickness. In some examples, the sheet material may have an average thickness in the range of about 0.05 mm to about 2 mm or more, sometimes about 0.1 mm to about 1 mm, and other times about 0.3 mm to about 0.5 mm, exclusive of any adhesive or other supporting structures. In examples wherein the sheet material comprises a non-uniform thickness, the sheet material may comprise an edge region with reduced thickness relative to an interior region with an increased thickness. The transition between the reduced and increased thickness regions may be smooth or angled, and in some variations, three, four, five or more regions of different thicknesses may be provided. In other examples, the regions of reduced and increased thicknesses may be arranged in other configurations, such as those depicted in FIGS. 24 and 25, which are described in greater detail below. In some variations, the sheet material may be attached or embedded with other reinforcement structures, or may comprise a woven or braided sheet configuration. The sheet material may be manufactured in any of a variety of shapes, and may be further cut or shaped during manufacturing, or at the point-of-use, to another shape and/or size. The shapes include but are not limited to circles, ellipses, ovoids, squares, rectangles, trapezoids, triangles, arcuate shapes, starburst shapes, and the like. The corners of the shape, if any, may be rounded or angled.

The dressing 101 also further comprises an adhesive layer located on the lower surface 107 of the dressing 101. In some embodiments, the thickness of the adhesive may be increased to facilitate placement and resist wrinkling that may lead to dressing wrinkling and seal leaks. In one embodiment of the dressing, the adhesive dressing thickness is increased to thicknesses substantially in the range of about 300 microns to about 10,000 microns or more, sometimes about 500 microns to about 2000 microns, and other times about 500 microns to about 1000 microns. Typical dressings used for RPWT may utilize thin relatively inelastic polyurethane film backings or facestock on the order of about 25 microns to about 50 microns in thickness with acrylic adhesive layers on the order of about 25 microns to about 125 microns in thickness. These thicknesses are demonstrably not sufficient in practice to easily create air-tight seals that last for about 4 to about 7 days. These thinner dressing may produce air leaks more often than when dressings with thicker adhesives were utilized. In addition, wrinkling with application of the thicker dressing was also reduced due to the increased rigidity afforded by the dressing thickness.

In some further examples, the adhesive layer material may be selected to provide an initial 90°-peel release force in the range of about 5 N to 18 N for a about 25 mm wide specimen. In some variations, the release force may be in the range of about 0.2 N/mm to about 1.5 N/mm, sometimes about 0.4 N/mm to about 1 N/mm, and other times about 0.5 N/mm to about 1.2 N/mm. The procedure for measuring the release force may be a standardized procedure, such as ASTM D3330, or other appropriate procedure. The adhesive layer may also be selected to provide a probe tack force property in the range of about 2.75 N to about 5 N with an initial loading of about 100 kPa, or other times in the range of about 2 N to about 6 N. The probe tack force may also be measured using standardize procedure, such as ASTM D2979, or other appropriate procedure. In some further embodiments, the adhesive layer may be selected to exhibit a decreased release force of about 20%, about 30%, about 40%, or about 50% or higher over a period of about 24 hours, about 48 hours, about 72 hours, or about 96 hours. In some instances, a reduced adhesive force over time may facilitate periodic dressing removal while reducing adhesive related damage to the surrounding skin.

In additional embodiments, fluid absorption of the dressing may be increased with adhesive material selection and thickness. For example, in some embodiments the dressing is composed of a hydrocolloid. In some examples, a different skin adhesive is provided around the edge or periphery of the dressing, while a hydrocolloid layer is provided on the interior region of the lower surface of the dressing. In other examples, however, the hydrocolloid may function both as a fluid absorption layer and an adhesive layer. The compositional properties and increased thickness of the dressing adhesive element allow for more capacity to handle fluid absorption, which may be beneficial in having a dressing that is functional in the presence of wound exudates and additionally promotes wound healing by maintaining a moist environment.

The dressing system may also comprise adhesion strength gradients on the undersurface of the dressing. In some examples, adhesive with higher bonding strength at the periphery of the dressing is provided compared to the central portion of the dressing. This is particularly important for RPWT treated wounds with fragile surrounding skin or smaller peripheral satellite wounds. Since the central portion of the dressing may be closest to the RPWT treated wound, the lower adhesive bonding properties of the central portion of the dressing may be less traumatic upon removal to the more delicate peri-wound skin and satellite lesions. The increased adhesive strength along the periphery may serve to maintain the integrity of a seal in a nonlimiting manner by mitigating lifting of dressing edges, disruption from moisture (i.e. sweat, bathing, etc.).

In further embodiments, a dressing with adhesion strength characteristics that decrease over time is disclosed to allow for sufficient sealing characteristics between dressing changes and easier and less traumatic removal of the dressing at the desired time of dressing change. In some embodiments, the dressing adhesive may have decreased bonding strength over time to allow for maximum adhesion during the period of treatment with RPWT between dressing changes, but weakened adhesion at the time of dressing change (typically in about 3 to about 7 days). This again allows for lesser trauma to the peri-wound skin during treatment. In some embodiments, the dressing is a hydrocolloid dressing that has a weakening bond to the underlying skin with water absorption overtime. An indicator in the dressing may further indicate when the dressing should be removed and/or replaced. In additional configurations, the adhesive element may be deactivated or weakened with temperature, moisture, light, solution or other related modality that can weaken adhesive bonding.

A dressing with a thicker central dressing and a thinner peripheral dressing and backing system for simplified application is also disclosed. In this embodiment, a two seal system may be implemented to mitigate air leaks that may occur from the dressing to the wound bed in which a thicker dressing is bordered by a thinner dressing that extends around the edges of the dressing to create a secondary seal. In some embodiments, the central dressing may be made of a thicker hydrocolloid dressing and the peripheral dressing is a thinner polyurethane border with a stronger adhesive profile than the central hydrocolloid portion. The thinner peripheral second seal may help create a more resilient seal because the thinner portion of the dressing is less likely to curl or become mechanically disrupted than the thicker central portion. By combining the thicker and thinner dressings into a single dressing, the disclosed dressing captures the advantages of the thicker dressing as described above without the disadvantage of dressing edge curling and increased susceptibility to mechanical disruption. In addition, the second peripheral thinner dressing creates a second seal around the dressing that further mitigates the risk of air leaks in the dressing system. The use of adhesion gradients with the two seal system allows for robust seal at the edges with less traumatic removal to the peri-wound skin as well. In some embodiments, the dual-sealant system may possess two adhesive release liners. First, the central adhesive release liner is removed, and the dressing is placed on the patient. Next, the second release liner for the outer layer dressing, in some configurations a strip of liner along the dressing border, is removed after the central portion is adhered to create a secondary seal. In some embodiments, the double dressing has a peripheral portion of the dressing having a higher adhesive property than the central portion of the dressing to prevent the edges of the thicker central layer from curling up while minimizing trauma to the peri-wound skin.

An absorptive dressing is further disclosed that prevents maceration of the underlying skin and promotes a moist wound healing environment for skin wounds around the primary wound treated with RPWT. Disclosed herein is a RPWT dressing with moisture absorbent properties that augments wound healing conditions by reducing moisture build-up at the peri-wound skin and satellite lesions around the main lesion being treated with RPWT. This dressing in some embodiments is a hydrocolloid dressing or dressing with similar characteristics as a hydrocolloid. In some variations, the hydrocolloid layer (or other moisture absorbent material) may have an absorbency rate of about 900 grams/m$^2$/day, about 1000 grams/m$^2$/day, about 1100 grams/m$^2$/day, about 1200 grams/m$^2$/day, or about 1500 grams/m$^2$/day or higher. The advantages of using an absorptive dressing as a dressing are that it can prevent maceration of the underlying skin, it is in contact with, and it can act as a good wound dressing for satellite lesions without the need for other secondary dressings underneath the dressing. In this embodiment the dressing itself may serve as the dressing for the peri-wound skin and peri-wound satellite lesions. The adhesive dressing disclosed in some embodiments may also contain therapeutic agents including drugs that facilitate healing or antimicrobial agents such as silver. One of the principles of modern wound therapy is the benefit of maintaining a moist wound healing environment. Thus, dressings for wounds that maintain a moist wound healing environment have become the mainstay of treatment for many types of wounds. Dressing such as alginates, hydrocolloids, and foams, all have absorptive properties that optimize the moisture levels of the underlying tissue for healing. Traditional RPWT dressings are not optimized for promoting healing of fragile peri-wound skin and satellite lesions. If the environment under the dressing near the underlying skin or satellite wounds is wet, it can lead to maceration of the underlying skin and wound edges. If the wound environment is dry, it can lead to suboptimal wound healing. A moist wound environment may be provided by moist gauze or other moist wound contact material. In some examples, the moist gauze is used in combination with a hydrocolloid dressing to provide a moist wound environment while wicking away moisture from the peri-wound skin.

A breathable dressing is disclosed that prevents maceration of the underlying skin. In some embodiments, the dressing will be configured to have a high enough moisture vapor transfer rate (MVTR) to allow for vapor loss that minimizes fluid collection over the peri-wound skin and the development of maceration of the underlying skin while at the same time maintaining a sufficiently strong seal to deliver RPWT. In one embodiment, the dressing comprises a hydrocolloid layer with an incorporated breathable component or construction. The hydrocolloid layer may be paired with a cover material that is also configured to wick away moisture, and in some variations, may have a MVTR of about 900 grams/m$^2$/day, about 1000 grams/m$^2$/day, about 1100 grams/m$^2$/day, about 1200 grams/m$^2$/day, or about 1500 grams/m$^2$/day or higher. In some embodiments, the combination of moisture absorption and MVTR afford the dressing the ability to maintain desirable moisture content at the wound bed while reducing maceration and damage of peri-wound skin. In other examples, the dressing may comprise a single layer of hydrocolloid or hydrogel.

In some examples, the adhesive layer may be configured to mitigate pain and discomfort encountered by patients during the placement and replacement of reduced pressure therapy dressings. Damage to underlying tissue may also be reduced. The dressing may comprise an adhesive coating that creates bonding that is amenable to softening through a chemical reaction caused by application of a removal solution or hot air. In another embodiment, the adhesive coating may comprise a resin that softens when irradiated with ultraviolet (UV) radiation. Examples of a UV-softening adhesive include adhesives that have a bond which is broken by irradiation of an ultraviolet ray, such as CH, CO(ketone), CONH(amide), NH(imide), COO(ester), N=N(azo), CH=N(Schiff) and the like. An adhesive predominantly containing such a bond may be employed, for example a polyolefin adhesive such as a polyethylene adhesive or a polypropylene adhesive, a polyimide adhesive, a polyester adhesive, a polymethylmethacrylate (PMMA) adhesive and on the like. Also, an adhesive containing aromatic hydrocarbons (one or a plurality of benzene rings, or a fused ring thereof) in its structural formula may be employed. For example, some examples may employ an adhesive of a polyphenylenesulfide (PPS) adhesive, or of a polyethersulfone (PES) adhesive. Also, one or a combination of two or more of these materials may be employed. These adhesives may improve patients' quality of life as pain and re-injury during dressing changes would be mitigated and treatment time may be shortened. Finally, the adhesive coating may be pressure sensitive or otherwise formulated to permit long term robust adhesion to skin.

The treatment system 100 may further comprise a port 102 coupled to tubing 103 that provides a fluid communication conduit from underneath the dressing 101 towards a reduced pressure source (not shown). Port 102 may comprise compliant materials and a low vertical profile. In some examples, the low vertical profile comprises a maximum perpendicular dimension to the sheet material 101 that is smaller than a maximum transverse dimension to the maximum perpendicular dimension, an optionally transverse to the longitudinal axis of the tubing 103. In some examples, the maximum transverse dimension may be twice, three times, four times, five times, or six times or more greater than the maximum perpendicular dimension of the port 102. In examples wherein the port is integrally formed with the dressing materials, these dimensions may be measured from the plane aligned with the upper surface of the dressing.

In some examples, tubing may be attached or separated from the port using a connector fitting located on the port. The fitting may be configured to accept a cut tubing end, or may be configured to attach to a complementary end connector fitting that is attached to the tubing. In still other examples, the tubing may be integrally formed with the port. In still other examples, all or a portion of the port may further be configured to be detached and reattached to the dressing.

As depicted in FIG. 1, in some examples, tubing 103 may further comprise one way flow mechanism 105. In some examples, the one way flow mechanism may reduce the risk of contaminated wound aspirate to backflow back into the wound. The one way flow mechanism may also permit detachment of the vacuum source without backflow of gas back into the treatment site. As mentioned previously, in some examples, multiple one way flow mechanisms may be provided along a flow pathway. In other embodiments, one way flow mechanism may be incorporated into port, or the vacuum source attached to the one way flow mechanism.

Figure 2:
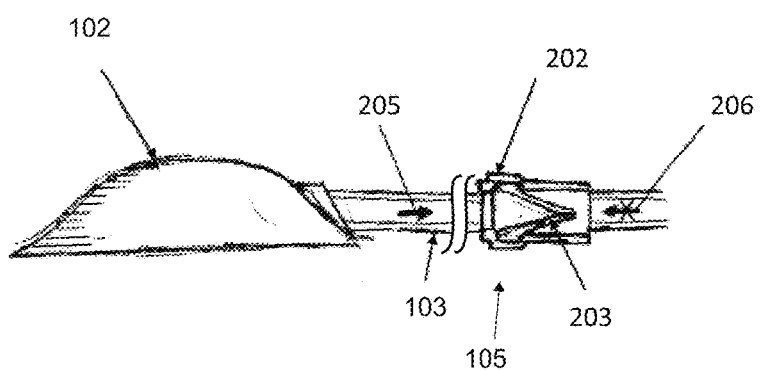
FIG. 2 is a schematic side elevational cut-away view of a connector configured for use with a vacuum source.

FIG. 2 is a schematic cut-away view of the port 102 and one way flow mechanism 105 depicted in FIG. 1. As shown, the one way flow mechanism 105 may comprise a valve 203 encased in housing 202 which is interposed in tubing 204. Valve 203 as depicted in FIG. 2 is a duckbill valve, but in other examples the flow mechanism 105 may comprise other valves previously mentioned or any other valve known in the art. Valve 203 may be oriented such that forward flow 205 of material is permitted towards the reduced pressure source. Forward flow 205 may comprise wound drainage fluids (exudates) or other material which is desirous to evacuate toward the reduced pressure source. In case reduced pressure application is terminated or interrupted, backward flow 206 of material may occur towards the port 102, but may be prevented or reduced by the one way flow mechanism 105.

Figure 3A:
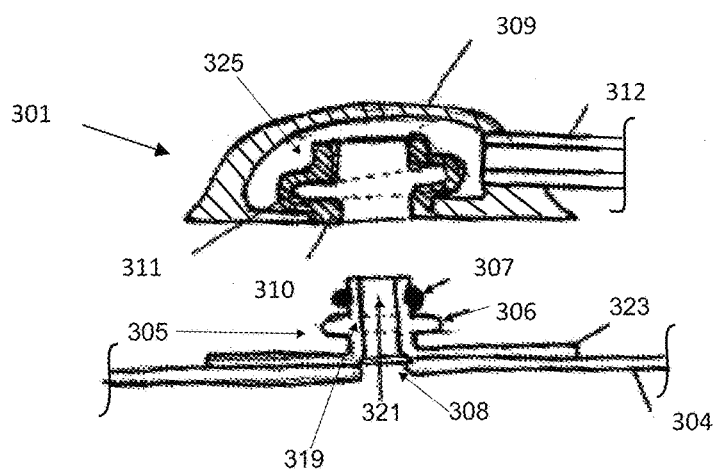
FIG. 3A is a cross-sectional component view of the port assembly in FIG. 2.
Figure 3B:
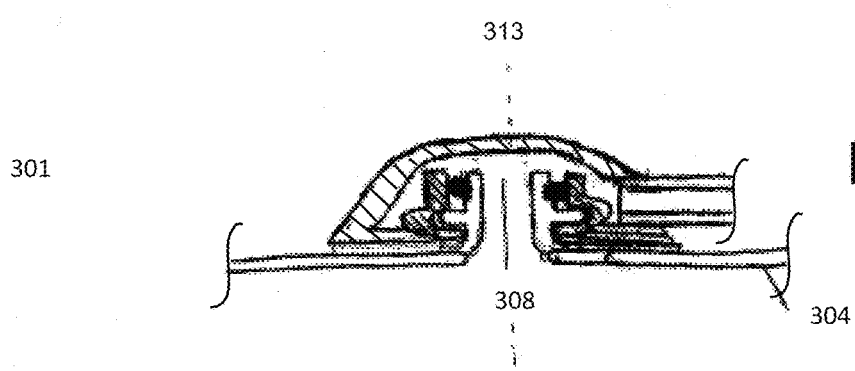
FIG. 3B is a cross-sectional view of the port assembly of FIG. 3A in assembled configuration.

Referring to FIG. 1, in some examples, the port 102 may comprise a port assembly that permit partial or full rotation of movement relative to the dressing 101. Here, port 102 is configured to with a range of rotational motion 104 around a rotational axis 108 that is generally normal to the plane of the dressing 101. Movement of the port may facilitate placement of the dressing 101 and/or securing the vacuum source. Port motion may also reduce the risk of kinking of the tubing 103, or transmission of torsional forces between the vacuum source and the dressing, which may improve patient discomfort or reduce the risk of dressing separation from the treatment site. FIGS. 3A and 3B depict one example of a rotatable port assembly 301. Port assembly 301 comprises a base or collar member 305 that is adhered or attached to the upper surface 315 of the dressing 304 at a lower plate or flange 323, but in other variations, the collar member may be adhered or attached to the lower surface 317 of the dressing 304, or both surfaces 315 and 317. Port assembly 301 further comprises a port body 309 that attaches to the collar member 305. The collar element 305 and the port body 309 may comprise flexible, semi-flexible or rigid materials. In some variations, the collar element 305 may comprise a material that is more rigid or otherwise has a greater durometer than the material comprising the port body 309. An opening or fenestration 308 through dressing 304 communicates with a lumen 321 of the collar element 305. The collar element 305 further comprises a rotational axle 319 that comprises a circumferential ridge 306 and an o-ring 307. When the port body 309 is coupled to the collar element 305, the rotational axle 319 is retained in a port cavity 325 by a port flange 327 that forms an interfit between the circumferential ridge 306 and the lower flange 323. The lumen 321 of the collar element 305 provides fluid communication between the fenestration 308 of the dressing 304 and the port cavity 325 at any angle of the port body 309. In other examples, the lumen of the port assembly may be configured as a side lumen whereby certain angular positions of the port body may seal off the lumen, thereby permitting the rotation of the port body as an open/close valve.

In the example depicted in FIGS. 3A and 3B, the tubing element 312 is may be bonded or glued or otherwise permanently sealed to the port body 309. In other variations, however, the port body may comprise a recessed or projecting flange configured to sealably insert into the lumen of a tube. The port body may be configured to attach to the tubing at any of a variety of angles relative to the plane of the dressing. In the depicted embodiment, tubing element 312 is directed parallel to plane of dressing 304. In other embodiments, tubing element 312 may directed at any angle between about 0 degrees and about 90 degrees relative to dressing 304, or may comprise at least partial rotational degree of freedom which allows alteration of angle between tubing element and dressing in the range of about 0 degrees to about 90 degrees. An anti-kink structure may be provided on the port body or the tubing to resist kinking of the tubing at the port interface. In some variations, port body 309 may further comprise compliant or elastomeric materials, and may also comprise a reduced pressure indicator as described later. The port body 309 may further comprise a sleeve element 310 within the port cavity 325, configured to form a complementary interfit with the rotational axle 319. The sleeve element 310 may further comprise a circumferential groove 311 configured to accept the ridge 306 of the collar element 305. This may improve the sealing characteristics between the collar element 305 and the port body 309 by providing a longer tortuous pathway for gas to escape. The sleeve element 310 may also resist tilting movement of the port body 309 and the collar element 304, thereby providing additional stability that may further comprise radial groove 311 but is configured to permit rotation of port body 309 relative to dressing 304 along axis 313 substantially normal to dressing 304. When port 301 is assembled onto dressing 304, o-ring 307 may form an additional seal against sleeve element 310. As mentioned previously, port body 309 may further be configured to be simply detached and reattached to the substantially rigid collar element 305.

Figure 6A:
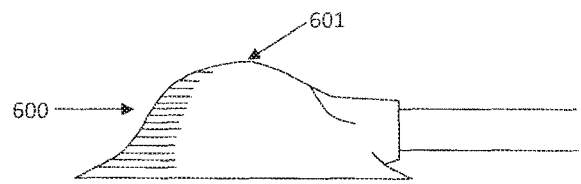
FIGS. 6A and 6B depict one example of a port assembly with a pressure indicator.
Figure 6B:
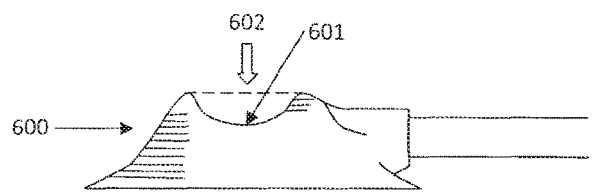

FIGS. 6A and 6B depict an optional feature of the port 600, comprising a reduced pressure indicator mechanism 601. The pressure indicator 601 may comprise a flexible membrane or a thinned region of the wall of the port body surrounding the port cavity, which is configured to substantially collapse or inwardly deform in the presence of a reduced pressure within the port (or port cavity of the port body). The degree of deformation at a particular relative level of reduced pressure may be tailored by varying the thickness of the flexible material or the type of flexible material. The indicators 601 may comprise the same or different material as the other portions of the port 600. FIG. 6A depicts port 600 in the absence of reduced pressure within the port 600, while FIG. 6B depicts the collapse of the pressure indicator 601 due the pressure differential between the higher atmospheric pressure and the reduced pressure within the port 600. Port 600 undergoes deformation 602 due to pressure differential, which visibly indicates the presence of reduced pressure. In some further example, color change materials that change color with mechanical deformation may be used for the pressure indicator 601. See, for example, the color change material described in U.S. Pub. No. 2006/0246802, which is hereby incorporated by reference in its entirety.

Figure 7A:
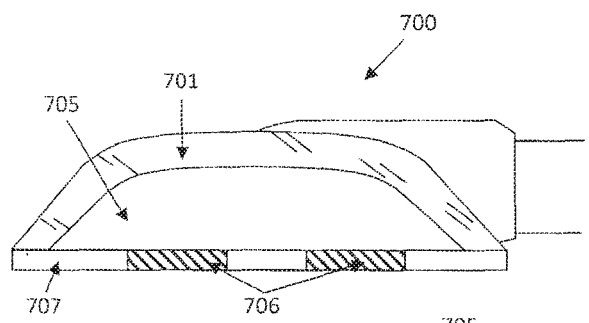
FIGS. 7A and 7B depict another example of a port assembly with a pressure indicator.
Figure 7B:
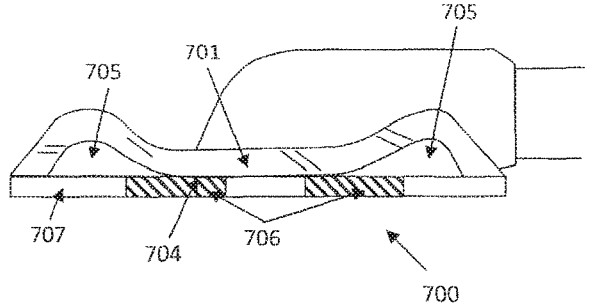

FIGS. 7A and 7B, illustrate another embodiment of a port 700 comprising a reduced pressure indicator 702. FIG. 7A depicts port 700 in an absence of reduced pressure, and FIG. 7B depicts port 700 in the presence of reduced pressure. The exterior wall 701 of port 700 is comprised of translucent, compliant material. Interior to the wall of port 701 is an empty volume 705 of air in fluid communication with a source of reduced pressure. Under application of reduced pressure, air in cavity 705 is evacuated, which causes a movable wall 701 of port 700 to collapse towards an inner wall or the floor 707 of port 700. Floor 707 further comprises one or more visually distinctive regions 706. In the absence of reduced pressure 702, the translucency of the wall 701 of port 700 obscures the visually distinctive regions 706. Under the presence of reduced pressure, the wall 701 of port 700 is biased towards floor 707 and contacts with distinctive regions 706. Direct contact 704 with distinctive regions 706 may cause distinctive regions 706 to become more visible through translucent wall 701 material. In some embodiments, distinctive regions 706 comprise regions of color or pigment. In some embodiments, distinctive regions 706 comprise symbols or patterns. In some embodiments, distinctive regions 706 may comprise text.

Figure 8A:
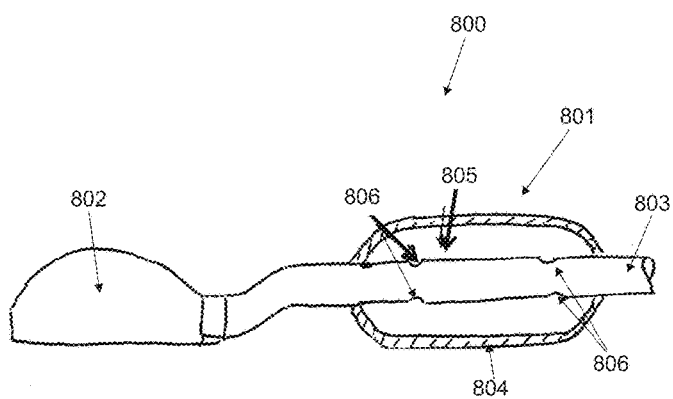
FIGS. 8A and 8B depict another example of a port assembly with a pressure indicator.
Figure 8B:
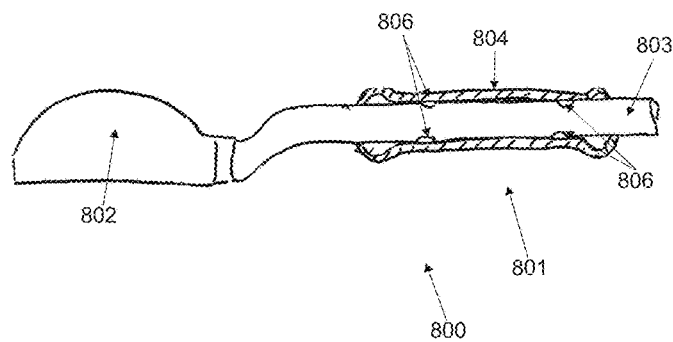

FIGS. 8A and 8B illustrate another embodiment of a reduced pressure treatment system 800 comprising a reduced pressure indicator 801. FIGS. 8A and 8B depict the reduced pressure conduit (e.g. the port 802 and the tubing 803) in absence of reduced pressure, in the presence of reduced pressure, respectively. The elastomeric material element 804 of the reduced pressure indicator 801 remains in an open or expanded configuration without the application of reduced pressure. In the presence of reduced pressure, the air in the elastomeric cavity 805 is evacuated through the communication openings 806 in the reduced pressure conduit tubing changing the configuration to a "sucked down" or collapsed configuration, where the elastomeric material of the indicator is pulled against the tubing. Although FIGS. 8A and 8B depict the pressure indicator 801 as having four communication openings 806, in other variations, the openings may number from about one to about twenty or more openings, sometimes about four to about sixteen openings, and other times about eight to about twelve openings. Direct contact of the elastomeric material with the tubing provides a physical and visual indication of reduced pressure. Direct contact may cause the outer surface of tubing 803 in the cavity 805 to be more visible through the elastomeric material 804 when the material is transparent or translucent. In some embodiments, the tubing in the indicator enclosure comprises regions of color or pigment. In some embodiments, the tubing in the indicator enclosure comprises symbols. In some embodiments, the tubing in the indicator enclosure comprises text. Although the elastomeric material 804 in FIGS. 8A and 8B comprises a sleeve or tubular shape that is adhered to the tubing 803 at the tubular ends 806 of the material 804, in other examples, the elastomeric material may comprise a sheet or cup-like structure adhered around its perimeter to the tubing 803. The elastomeric material 804 may be a silicone, polyurethane, and the like, and may be the same or different material that comprises the tubing 803.

Figure 9A:
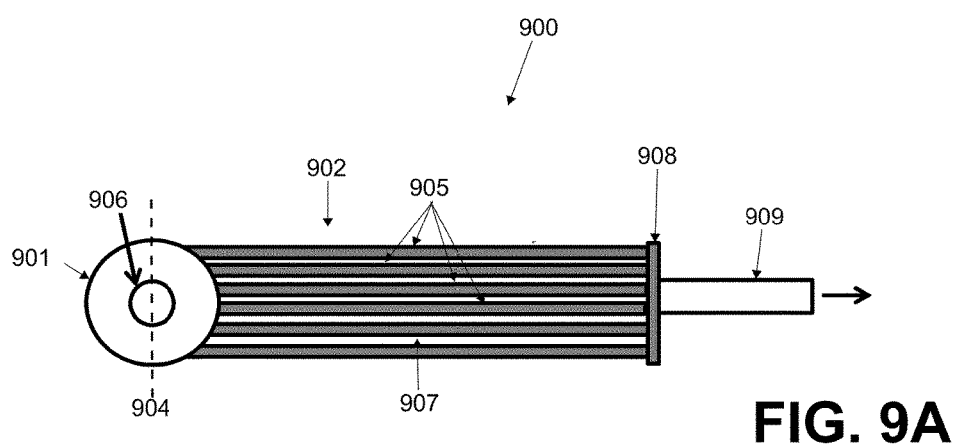
FIGS. 9A and 9B are superior and side elevational views of an example of a low profile port assembly.
Figure 9B:
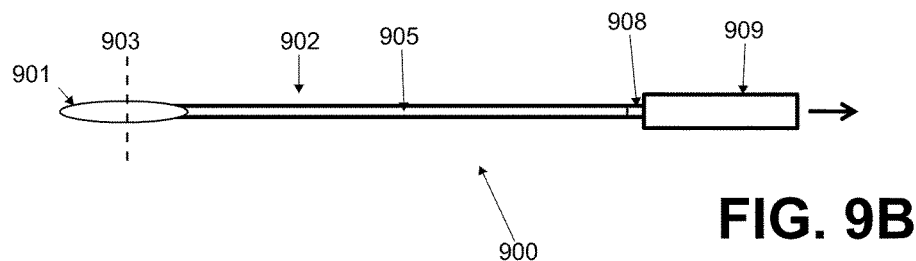

FIG. 9A illustrates a fluid communication conduit 900 comprising a low profile port 901 and low profile tubing 902 that has a reduced height 903 relative to an increased width 904. In some examples, the height 903 may be in the range of about 0.5 mm to about 30 mm, sometimes about 2 mm to about 15 mm, and other times about 4 mm to about 8 mm, while the width 904 may be in the range of about 0.5 mm to about 50 mm or more, sometimes about 4 mm to about 30 mm, and other times about 10 mm to about 15 mm. In some examples, the port may have a width to height 901 aspect ratio greater than 1:1 to reduce focal pressure concentration relative to ports having generally 1:1 ratios. The width to height ratio may be in the range of about 3:2 to about 20:1 or more, sometimes about 2:1 to about 10:1 and other times about 3:1 to about 6:1. The aspect ratio in the multi-lumen tubing 902 may be achieved using either a non-circular lumen or a configuration comprising multiple lumens 905, as shown in FIG. 9A. The opening 906 in the port 901 may be a single opening 906 that is in fluid communication with each of the multiple lumens 905. In other variations, each of the multiple lumens may have their own port opening. A web, membrane or other interconnecting structure 907 may be provided between the multiple lumens 905, but may be omitted in other variations.

The flexible multilumen tubing 902 is shown to be lower profile and to permit alternate channels of reduced pressure communication with the wound and removal of exudates. The port material and tubing may be made of one or more compliant materials such as silicone or other thermoplastics elastomers (TPEs) known to those in the art that are moldable, extrudable or otherwise formable. In some variations, due to the smaller lumen diameters, capillary resistance may significantly impact the movement of liquid materials through the port and/or tubing. To reduce these surface interactions, the port and/or tubing may be treated with a lubricious coating, and/or may undergo surface modification procedures to alter the hydrophilicity or hydrophobicity of the native port or tubing materials. Such procedures are well known in the microfluidics area. To facilitate standardized connections to various vacuum sources, a multiple lumen to single lumen adapter or connector 908 may be provided to attach to regular tubing 909. The connector 908 may also be integrally formed with the multiple lumens 905 and/or the regular tubing 909.

Figure 12:
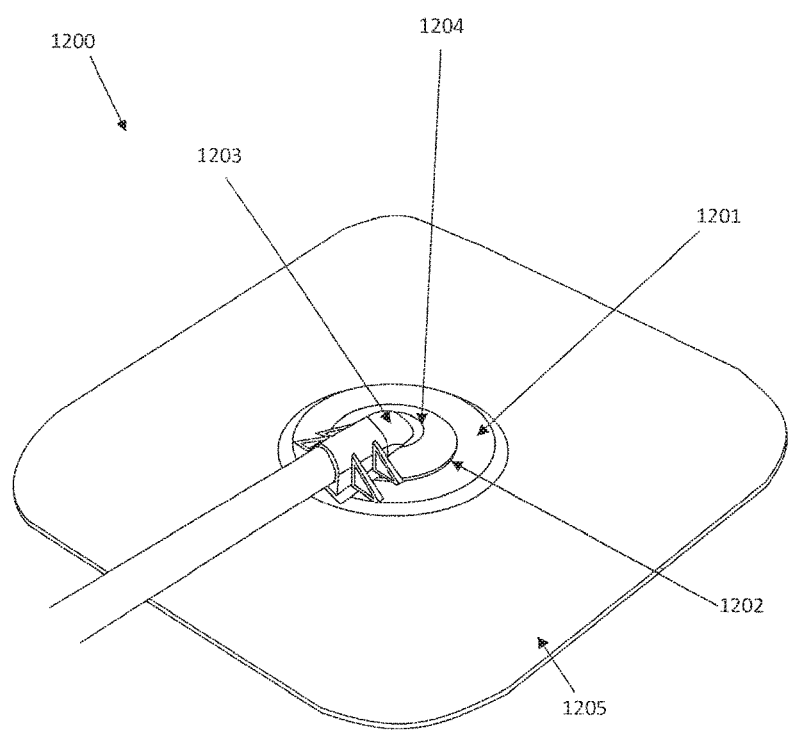
FIG. 12 is another example of a port assembly with a pressure indicator.

FIG. 12 depicts another example of a reduced pressure treatment device 1200 comprising a port member 1201 with an elastomeric membrane pressure indicator 1202 attached to a dressing 1205. In this example, the tubing attachment portion or connector 1203 of the port member 1201 is surrounded by a radial section 1204 of elastomeric membrane which deforms under pressure.

Figure 10A:
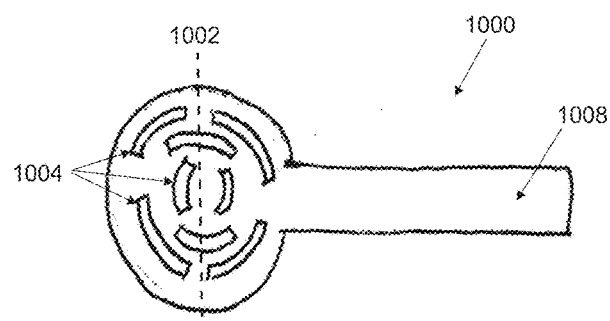
FIGS. 10A and 10B are superior elevational and side cross-sectional views of another example of a low profile port assembly.
Figure 10B:
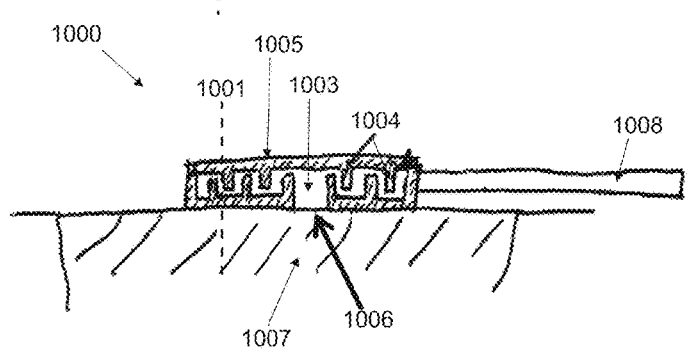
Figure 10C:
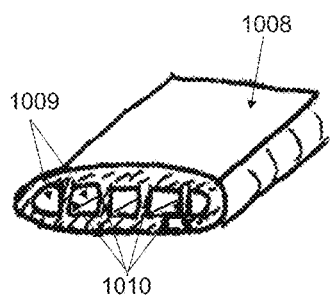
FIGS. 10C and 10D are perspective cross-sectional views of various examples of low-profile conduits of a low profile port assembly.
Figure 10D:
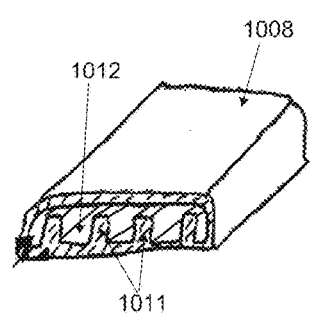

FIGS. 10A to 10D illustrate one example of the interior structure of a low profile port 1000, having a reduced height 1001 relative to its width 1002. In some example, with a reduced height 1001, the port cavity 1003 may or may not be at greater risk of collapse or closure, especially when manufacturing using a flexible material. To resist complete collapse, the cavity 1003 may comprise integrated supports 1004 to distribute loads and maintain cavity or conduit patency by preventing ore resisting collapse of the port walls 1005 and to maintain at least some patency with the port opening 1006 to the wound bed 1007 and the tubing 1008. Examples of various configurations for the low profile tubing 1008 are depicted in FIGS. 10C and 10D. In FIG. 10C, multiple lumens 1009 may be separated by lumen support walls 1010 that span from one internal surface to another, while in FIG. 10D, partial support walls 1011 located within and projecting into a single, non-circular common lumen 1012 are provided. The different support structure configuration may be used to distribute loads and may reduce or prevent collapse of the tubing structure when loaded.

Figure 11A:
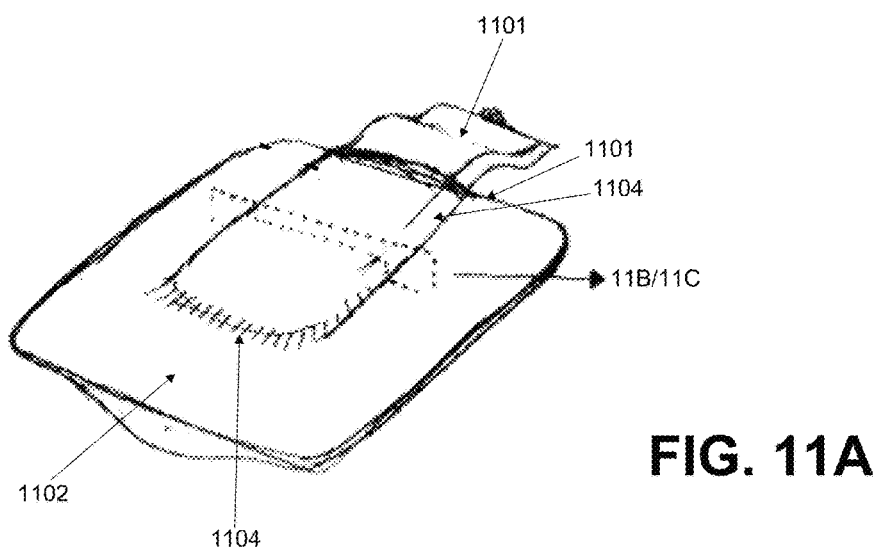
FIG. 11A is a perspective view of another example of a low profile dressing.
Figure 11B:
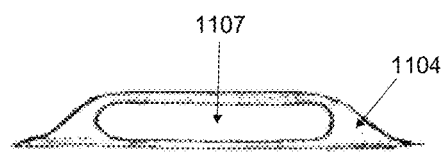
FIG. 11B is a cross-sectional view of the low profile conduit of the dressing in FIG. 11A.
Figure 11C:
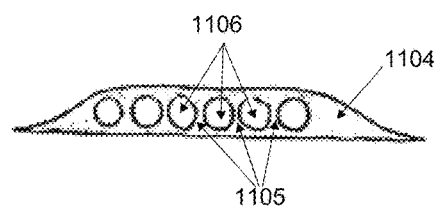
FIG. 11C is cross-sectional view of an alternate example of a low profile conduit.

FIG. 11A depicts another example of a low profile treatment device 1100 with low profile tubing 1101 directly integrated into the dressing 1102 itself. Unlike prior examples, the integrated tubing 1101 is attached to the dressing 1102 all the way to an outer edge 1103 of the dressing 1102. In other examples, the attachment of the tubing to the dressing may terminate anywhere in the range of about 1 cm to about 4 cm from the dressing edge, sometimes about 0.5 cm to about 3 cm, and other times about 0 cm to about 2 cm. To reduce the risk of the tubing 1101 snagging on clothing or other items, sloped edges 1104 may be provided. Integrated supports 1105 may be provided (FIG. 11C) to further help to distribute load bearing and/or maintain patency of the lumens 1106, but in other examples (FIG. 11B), the flat configuration lumen 1107.

Figure 13:
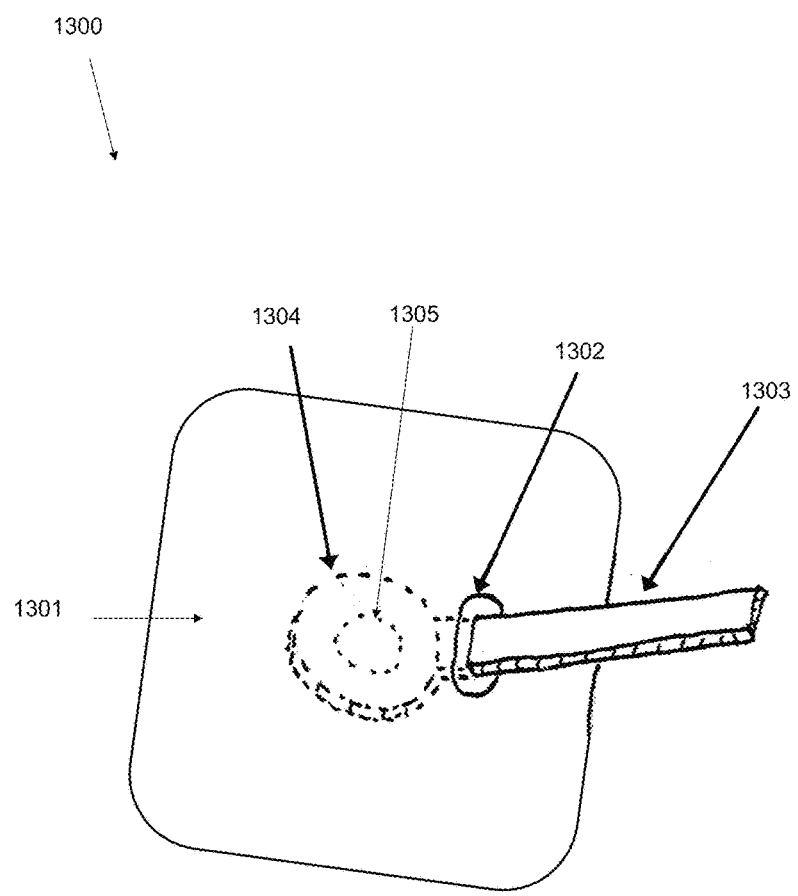
FIG. 13 is a schematic illustration of another example of a low profile port assembly.

FIG. 13 depicts another example of a reduced pressure treatment device 1300, comprising a dressing 1301 with a gasket or sealed junction 1302 through which low profile tubing 1303 passes through to an integrated suction port 1304. An air-tight junction permits the port to sit below the dressing and exit through the layer to the reduced pressure source. In this example, the port opening 1305 may directly communicate with the treatment cavity formed between the treatment site and the dressing. In other examples, the dressing may be a multi-layer sealing layer and the port may be located between two or more layers. In still other examples, the port may not be directly attached to the dressing 1301 but is permitted to pivot and/or translated through motion between the tubing and the sealed junction 1302 of the dressing 1301.

Figure 14:
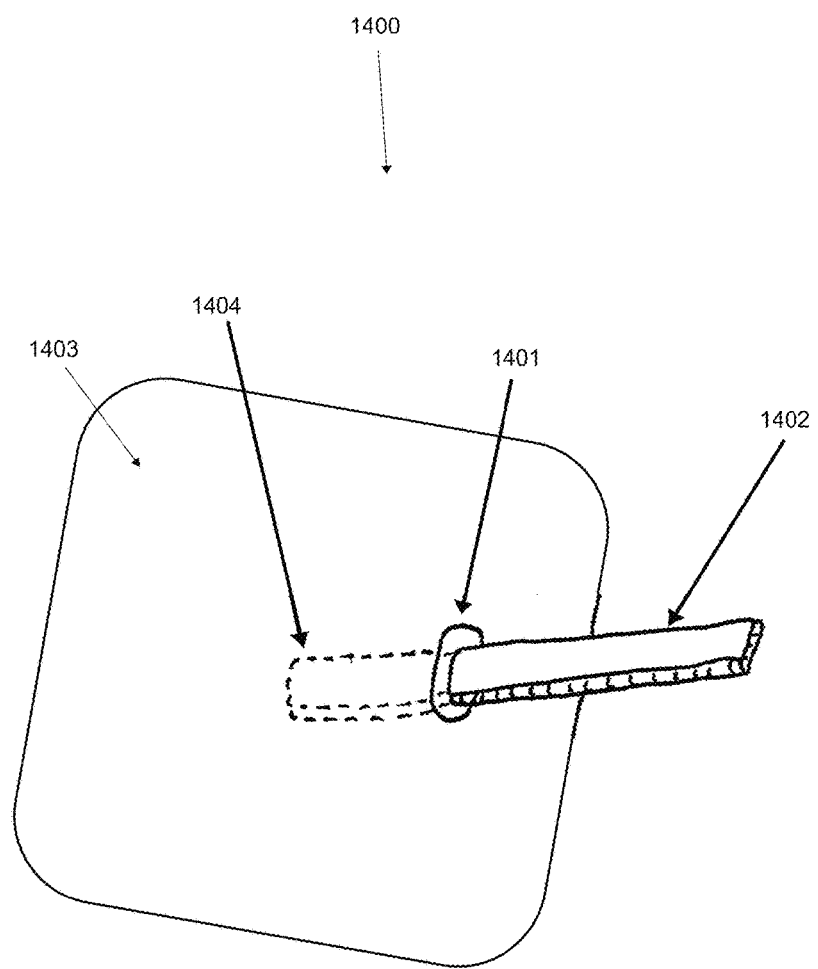
FIG. 14 is a schematic illustration of another example of a low profile port assembly.

FIG. 14 depicts another example of a treatment device 1400 comprising a sealed junction 1401 and a low profile tubing 1402 passing therethrough. In the examples, the distal end 1404 of the tubing 1402 is not attached to a port or suction head and may be customized in length to terminate at a desired location relative to the dressing 1403. In this configuration, both the dressing and reduced pressure conduit can be shaped (e.g. cut) to desired the geometry for a wound site. In some further examples, an attachable suction head or port may be coupled to the severed end of the tubing 1402 after customization. In still further examples, a puncture tool may be applied to the severed end of the tubing 1402 to form a plurality of side openings in the low profile tubing 1402 facing the treatment site, rather than solely rely upon the exposed lumen end of the low profile tubing 1402 for suction.

In some embodiments, the dressing comprises transparent material in at least a partial section of the surface to allow inspection of the wound, wound contact material or peri-wound skin under the dressing. In some embodiments, the dressing further comprises flaps which may be reversibly adhered to transparent sections of the dressing. These flaps may be substantially opaque or appropriately colored to cover and hide the underlying dressing and general wound region. In some embodiments, the dressing comprises a singular flap. In some embodiments, the dressing comprises a plurality of said flaps.

Figure 4:
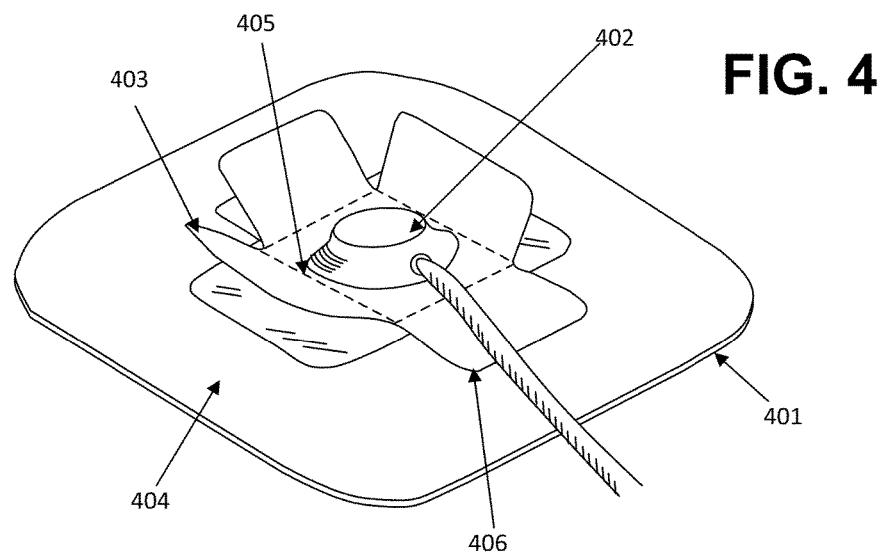
FIG. 4 illustrates another example of a dressing configured for use with a vacuum source.

FIG. 4 illustrates an example of a reduced pressure treatment system 400 configured to permit selective viewing under a substantially opaque dressing 401. Dressing 401 may be attached to port 402 as previously described. Dressing 401 further comprises opaque flaps 403 which cover substantially transparent regions 404 of dressing 401. Transparent regions may comprise polyurethane, silicone, transparent hydrocolloid, hydrogel, copolyester, polyethylene or any other substantially transparent material known in the art. Flaps 403 may further be releasably adhered to transparent regions 404 by a weak adhesion such as static adhesion, weak chemical adhesive or any other weak adhesive method known in the art. The dressing may also be configured to releasably adhere or attach to other portions of the sealant to maintain the flaps in a closed position during viewing or access. Flaps 403 may comprise hinge elements 405 to permit reversible adhesion to transparent regions 404 of dressing 401. Flaps 403 may also rest flush in a closed position 406 which occludes visibility of transparent regions 404. The depicted embodiment comprises a four-fold flap configuration oriented around port 402. In some variations, the flaps are configured to overlap beyond the borders of the transparent regions to facilitate grasping and lifting of the flaps. In these variations, one or more overlapping regions may be provided without any adhesive or weak adhesion properties.

Figure 5:
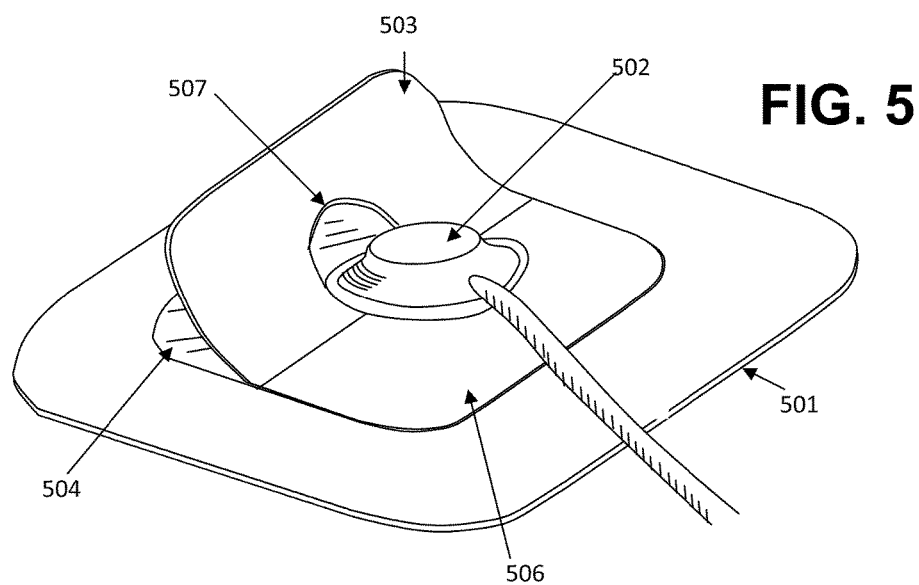
FIG. 5 illustrates another example of a dressing configured for use with a vacuum source.

FIG. 5 illustrates an alternate configuration of a bi-fold flap treatment system 500. Dressing 501 may be configured with a port 502 as described previously. Dressing 501 comprises opaque flaps 503 which cover transparent regions 504 of dressing 401 in the manner described in FIG. 4. Flaps 503 may further comprise cutout features 507 to accommodate geometry of port 502.

In some further embodiments, a dressing application system or reduced pressure treatment system further comprises one or more applicator elements located above and/or below the dressing to support and facilitate the application of the dressing to the desired body site, and may also improve air-tight sealing of the dressing to the body surface. One potential function of these applicator elements is to ease application by providing sufficient rigidity to the dressing such that it does not easily fold and buckle and consequently stick to itself when the adhesive layer is exposed. Secondly, when the dressing is applied, the dressing system may be held and grasped while avoiding contact with the adhesive elements of the dressing to permit simpler application to the desired surface. Third, the dressing system is customizable to accommodate specific anatomical contours. When the dressing system is shaped, for example, by cutting the dressing system, the functional elements that permit simple application of the dressing to a wound site are preserved.

In some embodiments of the dressing system, the dressing system includes at least one support layer that maintains sufficient system rigidity once an adhesive surface is exposed while a secondary element to the dressing system comprises a layer or series of layers that shield the user from inadvertent contact with the adhesive components of the dressing prior and/or during application. These elements serve to alleviate the existing problems with dressing application that lead to poor dressing seating characteristics such as the presence of wrinkles due to buckling and resultant channels in the dressing. The embodiments described herein are directed toward more effective adhesion of a dressing to a desired body site.

In one exemplary configuration, the support layer is releasably attached or adhered to the facestock of the dressing and can be detached from the dressing once the user deems appropriate such as after the dressing has been secured to the body site. This support layer may comprise a stiff carrier element that may be configured to include break lines or folds that facilitate easier lifting up of an edge of the material for simple removal. The positioning and design of the break line is also such that cutting of the dressing to a smaller size allows the break lines to remain accessible. This carrier element may be clear or translucent to facilitate visualization of underlying components of the dressing system and the body site to which it is attached provided the dressing is sufficiently clear or translucent. A polyurethane or other similarly conceived material with sufficient rigidity may be used as a carrier element. In another exemplary configuration, a paper stock may be used with a weak adhesive to provide support to the dressing. The break line may be introduced by kiss-cutting an already adhered carrier film on top of the dressing or cut prior to application to the dressing. The carrier may also comprise at least one opening, or window, that allows direct access to the dressing, and may be configured such that a conduit (e.g. a port and/or tubing) can pass through it to permit communication of reduced pressure to the volume below the dressing. The location of the break line in the carrier film may also configured to allow for ease of removal when a reduced pressure conduit such as a port and attached tubing are present on the dressing.

In another embodiment, separate or in combination to the support layer are elements attached to the adhesive element of the dressing are release handles that mitigate user interaction with the adhesive during application to prevent inadvertent adherence of the dressing to the individual applying the dressing. These handles can take the form of coated polymeric sheets folded back on themselves to allow simple removal after initial adherence of the dressing to the body site. The release handles may be transparent or translucent to permit visualization through a clear or translucent dressing and carrier or opaque. The handles may be formed from a laminated sheet such as a silicone treated paper, fluorosilicone, or fluoropolymer treated film for example. The folds of the handles may be spaced sufficiently close to the center of the dressing such that the fold that is not adhered to the dressing remains present even when the dressing is cut to a smaller size for customization. At least one of these release handles is oriented along the dressing surface, typically along the perimeter of the dressing. For example, two sets of opposing release handles may be positioned in such a manner to cover the edges of a rectangular dressing. Another element may also be present to cover and protect the adhesive between the release handles prior to dressing application. This layer similar to the release handles may be transparent or translucent to permit visualization through a clear or translucent dressing and carrier or opaque. The release liner may be formed from a laminated sheet such as a silicone treated paper, fluorosilicone, or fluoropolymer treated film for example. With the upper support layer and lower release handles elements in place, the stiffening and adhesive shielding aspects of the two elements are preserved even with dressing shape customization.

Figure 15:
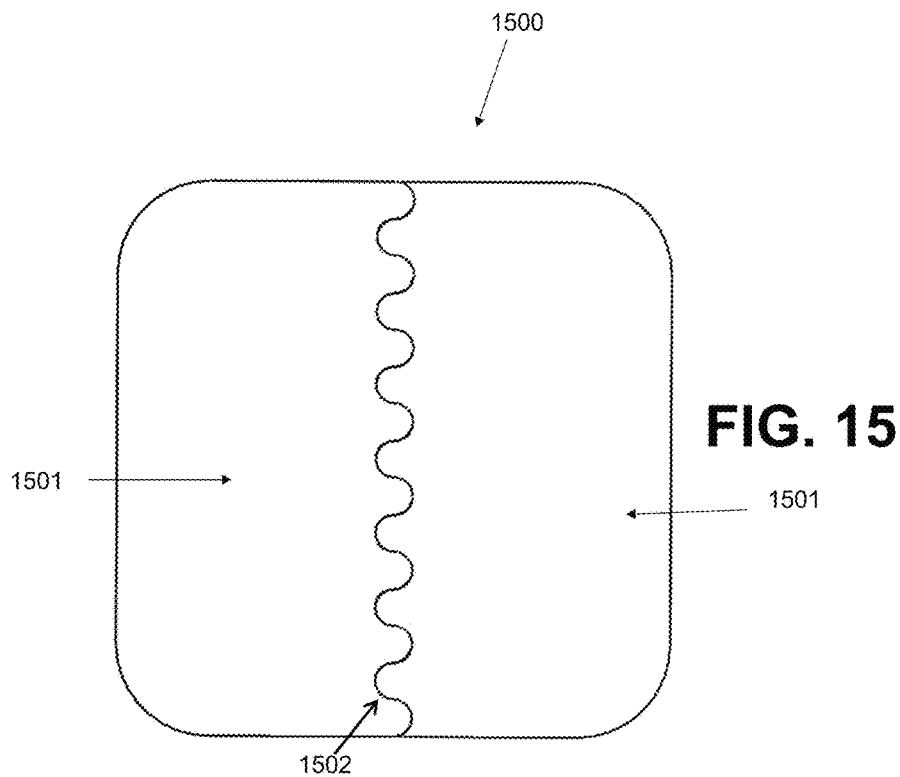
FIG. 15 depicts one example of a release linear configuration for the dressing illustrated in FIG. 1.
Figure 23:
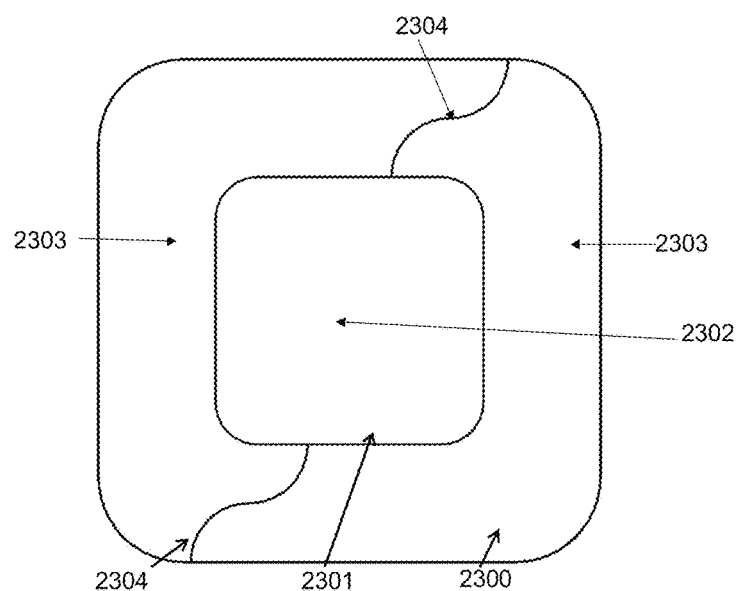
FIG. 23 depicts another example of a carrier layer configured for use with the dressing in FIG. 1.

FIG. 15 illustrates one example of a carrier element 1500 that may be used with a dressing or dressing. The carrier element 1500 may comprise a material and/or construction that has greater rigidity to help maintain the shape of the dressing during application or preparation. The carrier element 1500 may be releasably attached to adhesive layer or hydrocolloid layer located on the lower surface 107 of the dressing 101, but may also be configured for use on the upper surface of the dressing 101 by providing a central opening to accommodate the port 102. FIG. 23, for example, illustrates a carrier element 2300 with a central window region 2301 that allows exposure of the underlying dressing 2302 and to accommodate a port member or tubing. Curved break lines 2302 permit removal of the carrier subelements 2303 from dressing 2302. A translucent or transparent dressing may be provided to visualization of the underlying treatment site.

Referring back to FIG. 15, the carrier element 1500 comprises at least two subelements 1501 with a non-linear break line 1502 between them to facilitate lifting or separation of the subelements 1501 from the dressing 101. Although the break line 1502 depicted in FIG. 15 comprises a sinusoidal configuration, any of a variety of linear or non-linear configurations may be provided. In other variations, more than two carrier subelements may be provided, with two or more break lines that may be separate or branching. In still other examples, folded or overlapping tabs may be provided.

Figure 16:
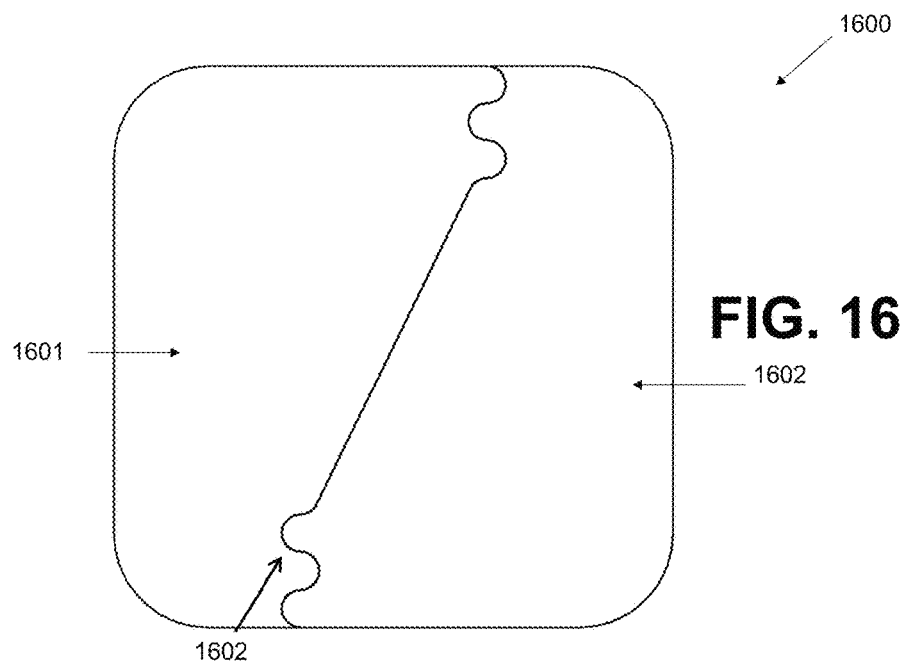
FIG. 16 depicts another example of a release linear configuration for the dressing illustrated in FIG. 1.

FIG. 16 illustrates an alternate configuration for a carrier element 1600 comprising two subelements 1601 with a break line 1602 having at least one segment 1603 that has a non-orthogonal orientation with respect to the closest edge 1604 of the carrier element 1600. The break line 1602 also comprises a linear segment 1603, which may or may not be the same as the non-orthogonal segment in every embodiment. When the carrier subelement 1601 is separated from dressing at the narrower region 1605, the peel force required for separation may be reduced as a result of the reduced contact width or transverse dimension to the direction of separation.

Figure 17:
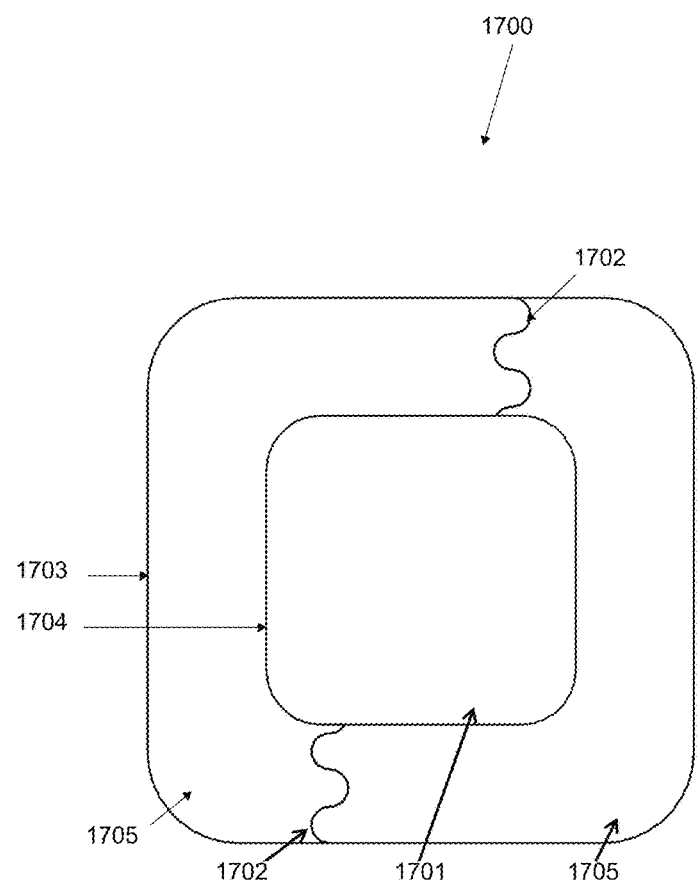
FIG. 17 depicts an example of a release linear configuration for the dressing illustrated in FIG. 1.
Figure 18A:
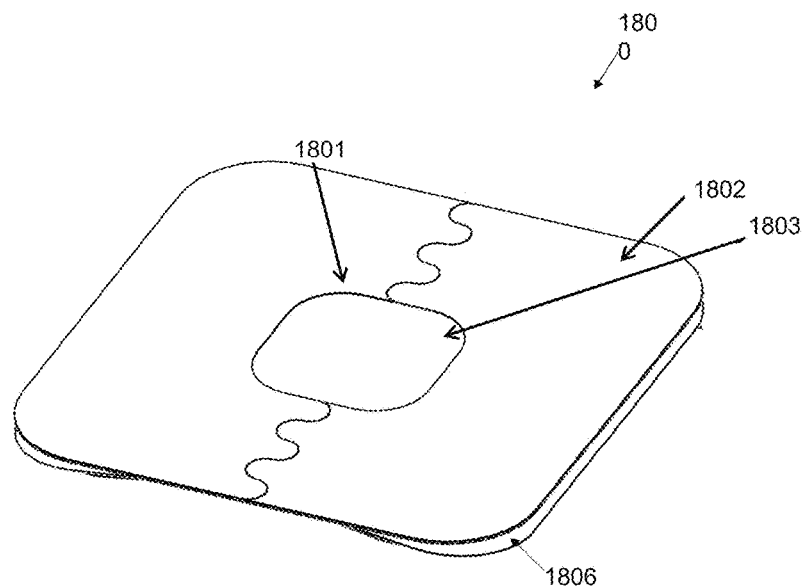
FIGS. 18A and 18B are superior and inferior perspective views of an example of a dressing comprising a carrier layer and multiple release layers.
Figure 18B:
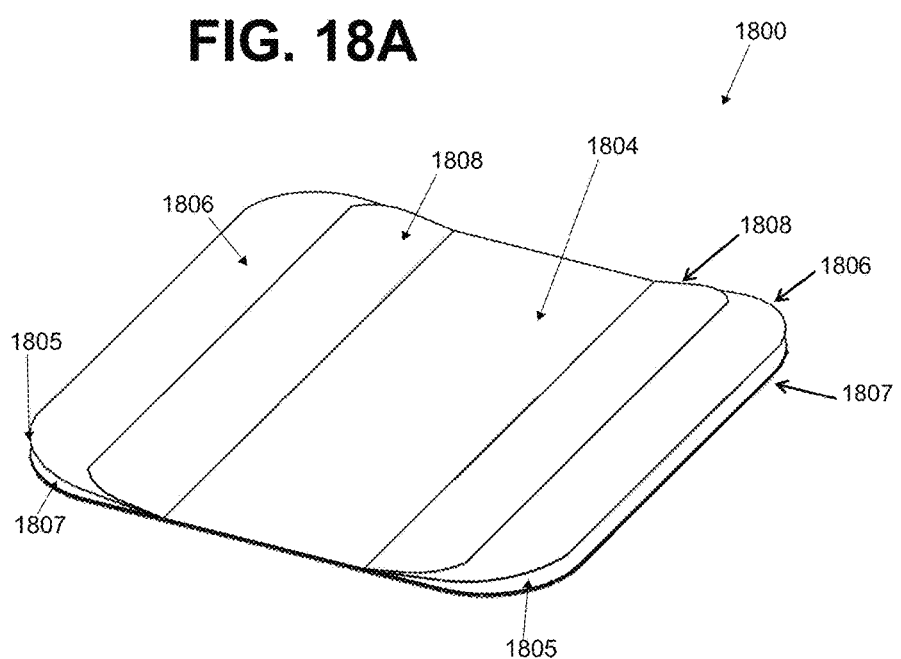
Figure 18C:
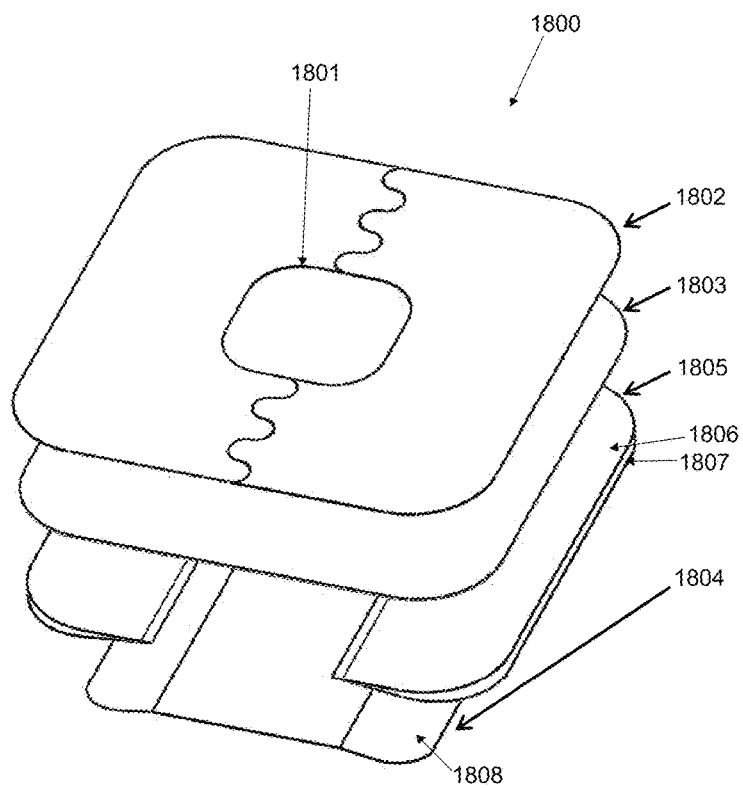
FIG. 18C is a expanded superior perspective view of the dressing in FIG. 18A.
Figure 18D:
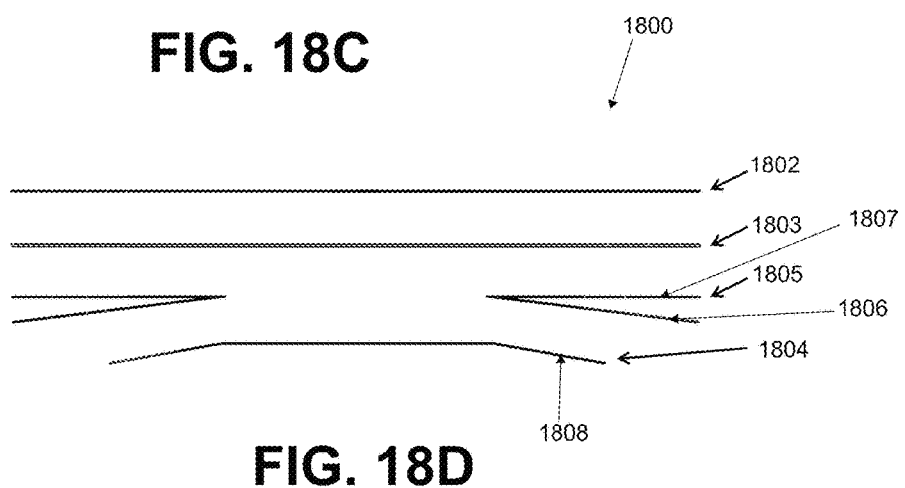
FIG. 18D is a schematic expanded side view of the dressing in FIG. 18C.

FIG. 17 illustrates another configuration for a carrier element 1700, comprising an interior or central window region 1701 that allows exposure of the underlying dressing elements. One or more break lines 1702 may be provided between an outer edge 1703 and an inner edge 1704 of the carrier element 1700. Where multiple break lines are provided, the break lines 1701 may be located at symmetrical locations to separate the carrier element 1700 into similarly sized and shaped subelements 1705, but in other variations, the break lines may be asymmetrically located.

FIGS. 18A to 18D illustrate a dressing system 1800 with a window 1801 in the carrier element 1802 to expose the underlying dressing or dressing 1803, and to accommodate a port (not shown) attached to the dressing 1803. The dressing system 1800 further comprises an interior release liner 1804, and two release handles 1805. The carrier element 1802 provides an increased stiffness and support to the dressing 1803 during application to a treatment site, while the window 1801 permits visualization of the treatment site to facilitate positioning of the dressing 1803. The interior release liner 1803 protects the adhesive layer of the dressing 1803 against inadvertent adhesion until the user detaches the liner 1803 prior to application. To expose the central portion of the dressing 1803, the free flaps 1808 of the interior release liner 1803 may be grasped to separate the liner 1803. The two release handles 1805 permit handling or grasping of the dressing 1803 without adhering to the adhesive layer on the lower surface of the dressing 1803. Once the exposed adhesive layer from the removal of the interior release liner 1803 is adhered to the desired treatment site, the free flaps 1806 of the release handles 1805 may be grasped and pulled to separate the adhered flaps 1807 of the release handles 1805 from the dressing 1803 to expose the remaining adhesive layer and permit complete adhesion of the dressing 1803 to the treatment site. Once the secured, the carrier element may be separated from the dressing 1803.

Figure 19A:
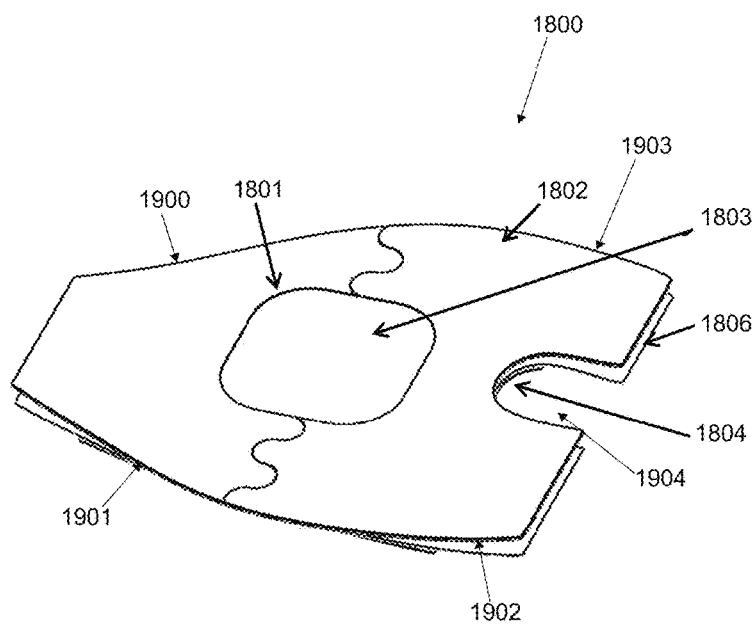
FIGS. 19A and 19B are superior and inferior perspective views of the dressing in FIGS. 18A and 18B following customized shaping.
Figure 19B:
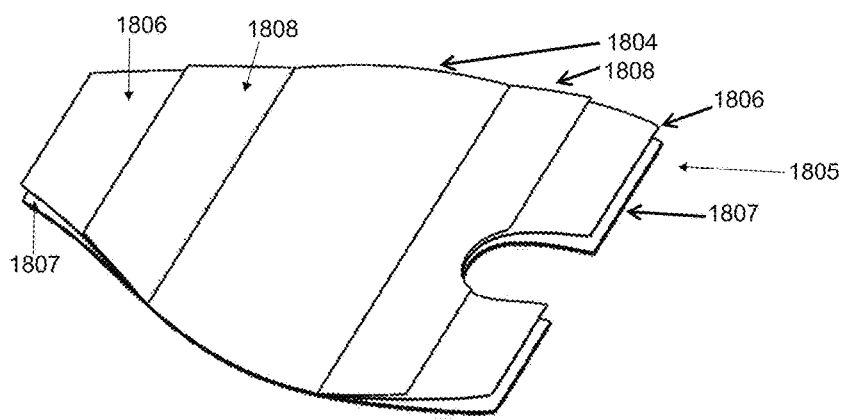

FIGS. 19A and 19B depicts the dressing system 1800 in FIGS. 18A to 18D after multiple cuts 1900-1904 were made to customize the system 1800 to a particular shape while maintaining its functionality. FIG. 19B is a perspective view of the underside of the dressing system 1800, illustrating that the release liner 1804 and release handles 1805 maintain their respective forms and functionality even after the dressing system 1800 and the dressing 1803 has been cut.

Figure 20:
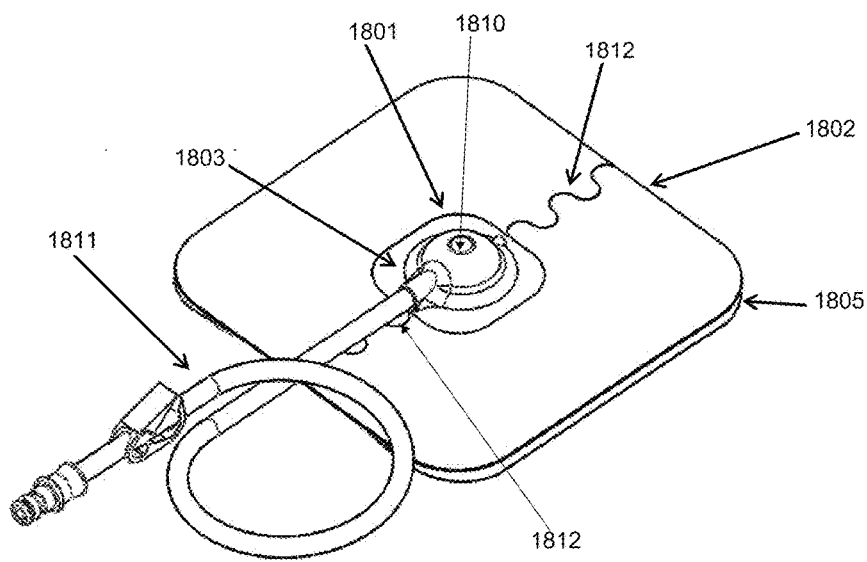
FIG. 20 depicts an example of the dressing in FIG. 18A with the port member and conduit.

For simplification purposes, FIGS. 18A to 18D depicted the dressing 1803 with the attached port member. FIG. 20, depicts dressing system 1800 in intact form, with the carrier element 1802 with carrier window 1801 surrounding the port assembly 1810 and tubing 1811 of the dressing 1803. Note that the break line 1812 in the carrier element 1802 is located in such a manner as to allow simple removal of the carrier element 1802 with the reduced pressure conduit present, e.g. minimizing interference from the port assembly 1810 and tubing 1811.

In further configurations of the device, reinforcements such as embedded rings or ridges may be incorporated into the dressing system. These structures or elements may streamline the application of reduced pressure dressings by mitigating buckling of the dressing and self-adherence of the dressing, and may also improve the ability of the dressing to form and maintain an airtight seal once it has been applied by reducing the wrinkling that may occur otherwise during application. In addition to dressing adhesive thickness, these elements may permit longer term delivery of reduced pressure to an area of tissue damage by providing a more robust seal with less ability to leak. Furthermore, the use of continuously running powered pumps to create reduced pressure may be obviated because the seal may be more robust than traditional RPWT dressings and may exhibit reduced or substantially no leakage. This type of treatment is less feasible using traditional reduced pressure sealant dressings.

Figure 21A:
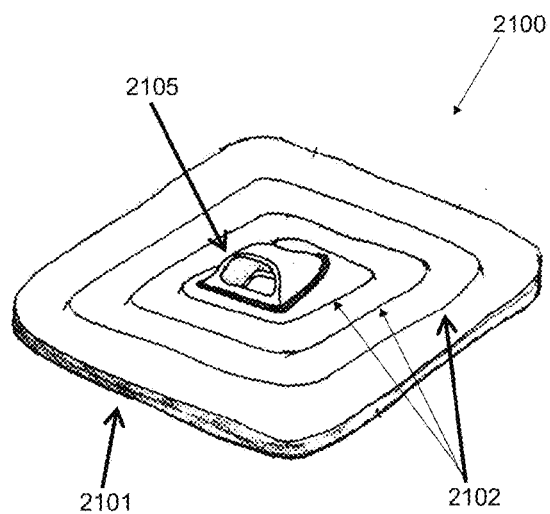
FIGS. 21A and 21B are superior and inferior schematic perspective views of an example of a reinforced dressing.
Figure 21B:
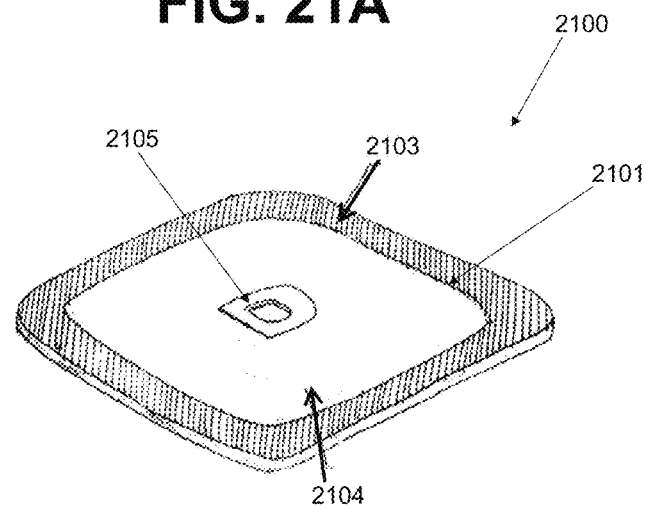

FIGS. 21A and 21B depict one embodiment of a dressing system 2100, comprising a thick adhesive layer 2101 (e.g. at least about 500 microns or greater) and circumferential reinforcement structures 2102 surrounding the port member 2105, which may reduce buckling/wrinkling of the dressing system 2100. Although each of the reinforcement structures 2102 in FIG. 21A comprises contiguous, closed configuration structures 2101, in other variations the structures may be segments and/or comprise a generally open configuration, e.g. C-shaped. In addition to the thick adhesive layer 2101, the dressing system 2100 further comprises a perimeter region 2103 with increased adhesive properties than the interior region 2104. In some situations, a more increased adhesion around the perimeter 2103 of the dressing 2100 may further helps to maintain dressing adhesion. In some variations, the difference in peel force between the perimeter 2103 and the interior region 2104 may be about 1 N to about 10 N for specimens about 25 mm in width, sometimes about 2 N to about 8 N, and other times about 1 N to about 4 N. The difference in probe tack force may be about 0.5 N to about 3 N with an initial loading of about 100 kPa, sometimes about 0.75 N to about 2 N, or other times about 0.5 N to about 1.5 N. In some further variations, the interior region 2104 may completely lack any adhesive. Other variations of the adhesive properties of the dressing were previously described herein.

Figure 22A:
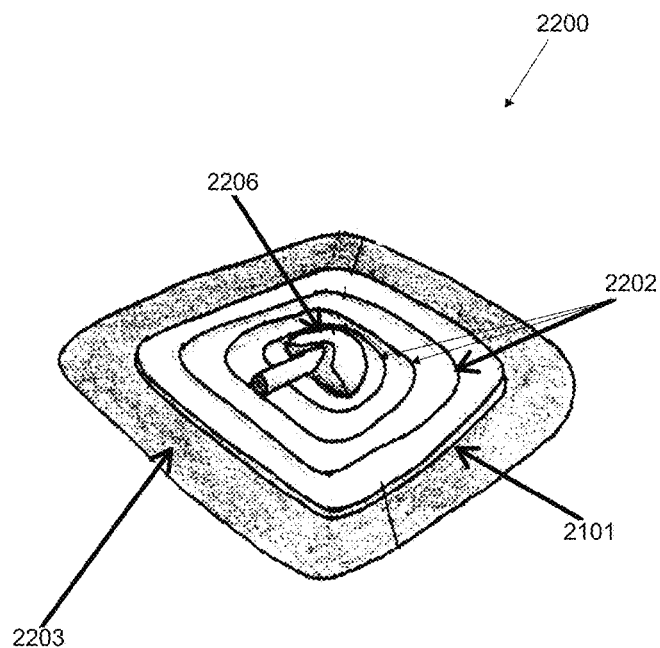
FIGS. 22A and 22B are superior and inferior schematic perspective views of another example of a reinforced dressing.
Figure 22B:
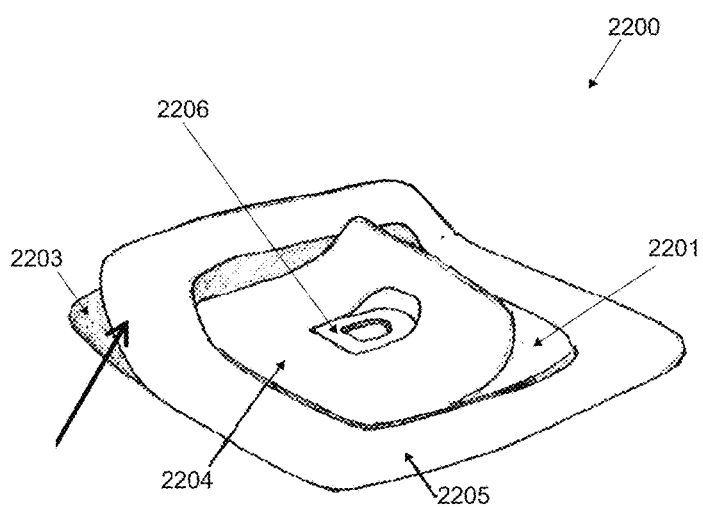

FIGS. 22A and 22B depict another example of a dressing system 2200 with a thick adhesive layer 2201 and radial reinforcements 2202 surrounding a port member 2206 to reduce buckling/wrinkling of the dressing. A thinner adhesive skirt 2203 around the perimeter of the dressing system 2200 is also provided. The thinner adhesive skirt 2203 may be tapered in thickness or may have a uniform thickness. The thinner perimeter also mitigates lifting of the dressing edge from the body surface. The dressing system 2200 may be applied by removing a central liner 2204 to expose the thick central adhesive layer 2201 first for application to the body surface, then a second perimeter liner 2205 is removed to expose and to adhere the adhesive skirt/border 2203.

Figure 24:
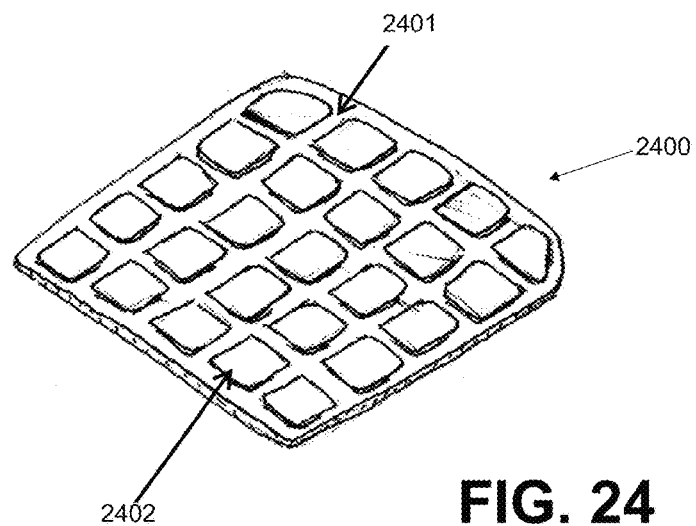
FIG. 24 is a schematic superior perspective view of another example of a reinforced dressing.

FIG. 24 depicts a dressing or dressing 2400 comprising relatively thicker and thinner regions 2402 and 2404 that may permit greater conformability of the dressing 2400 on the body surface. The thicker regions may be comprised of a thicker hydrocolloid adhesive material while the thinner areas may be comprised of thinner hydrocolloid or elastic polyurethane or other similar material. In some examples, the thicker hydrocolloid adhesive regions may have a thickness in the range of about 0.2 mm to about 2 mm, sometimes about 0.3 mm to about 1.5 mm, and other times about 0.5 mm to about 1 mm. In some further examples, the thinner hydrocolloid adhesive regions may be in the range of about 0.15 mm to about 1.5 mm, sometimes about 0.2 mm to about 1.2 mm, and other times about 0.5 mm to about 0.8 mm. The thickness ratio between thick regions and the thin regions may be in the range of the 1.2:1 to about 3:1 or more, sometimes about 1.5:1 to about 2:1 and other times about 1.3:1 to about 1:6:1. In this particular embodiment, the regions 2402 and 2404 are arranged or organized in an orthogonal grid fashion where the thick regions 2402 comprise square shapes. In other examples, the thick regions may comprise other shapes, e.g. circles, stars. etc., while in still other examples, the relationship between the thick and thin regions may be reversed, e.g. a waffle configuration wherein the thick regions comprise the grid lines and the thin regions comprise the square shapes.

Figure 25:
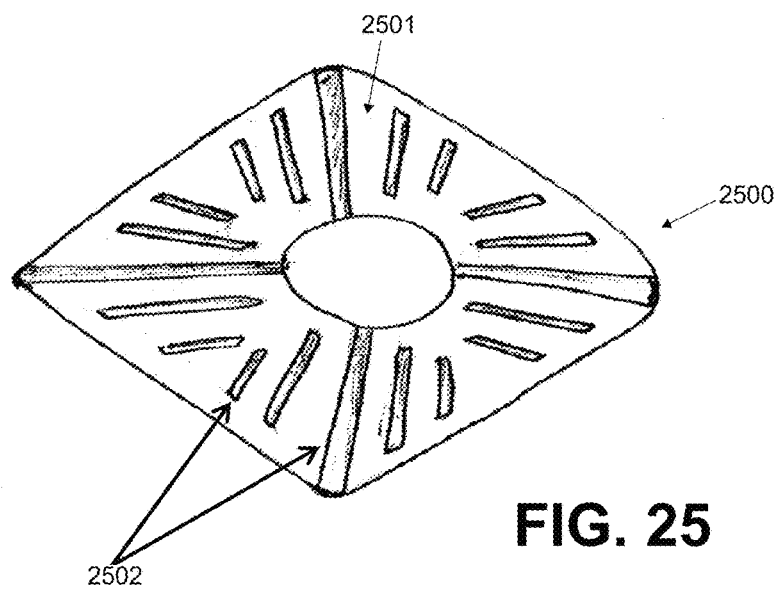
FIG. 25 is a schematic superior view of still another example of a reinforced dressing.

FIG. 25 depicts another example of a dressing 2500 comprising thick and thin regions 2502 and 2504 with the thin regions 2504 completely surrounding each thick region 2502 such that greater extension and stretch of the dressing 2500 may be permitted. The thicker regions 2502 may comprise linear members having a generally radial orientation relative to the center of the dressing 2500. As depicted in FIG. 25, the thick regions 2502 may have variable lengths and widths. The thick regions 2502 may comprise thick hydrocolloid adhesive material while the thinner regions 2504 may comprise of thinner hydrocolloid or elastic polyurethane or other similar material.

To further augment the leak resistance characteristics of the reduced pressure treatment system, a spray-on, paint-on or otherwise initially fluid-based dressing may be utilized. In some embodiments a flexible and/or adjustable dam, stencil, mask or containment apparatus that may be placed around the treatment site. The dam may be configured in multiple sizes and/or shapes for specific anatomic locations and in certain configurations has a soft, bottom edge that can conform to multiple body location sites to form a near fluid resistant seal. In certain embodiments, the dam is further equipped with a mechanism to hold a RPWT conduit. In some embodiments, the dam may be further equipped with a holder for a RPWT dressing (foam or gauze, or other). Upon positioning the dam around the wound, the dressing, which may comprise any of variety of fast curing polymers or other similarly behaving materials, is sprayed or otherwise applied over the treatment site to create an airtight seal and enclosure around the site, the dressing, and portion of the conduit in fluid communication with the site. In certain embodiments, the applied substance may be a fast setting silicone or latex. In some embodiments, a RPWT conduit may be applied after forming the airtight enclosure with the applied dressing. In such an embodiment, the user may create an opening in the applied dressing in order to attach the conduit. The opening may be pre-formed during spraying or formed after spraying. In some embodiments, the conduit is attached to the airtight enclosure with an adhesive. In some embodiments, the applied dressing may shrink about 1% to about 10% or more in size as it cures to draw the wound edges inward to promote faster wound closure/ wound healing. In other examples, a liquid dressing may be applied by brush, roller, or simply spread or squeezed over the treatment site.

Figure 26A:
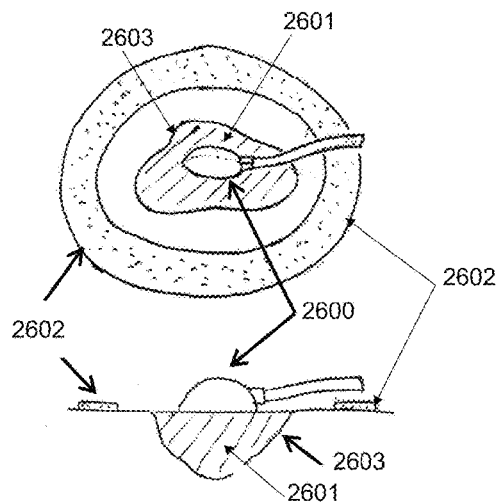
FIGS. 26A to 26C depict one method for sealing the dressing to a treatment site using a liquid sealant.
Figure 26B:
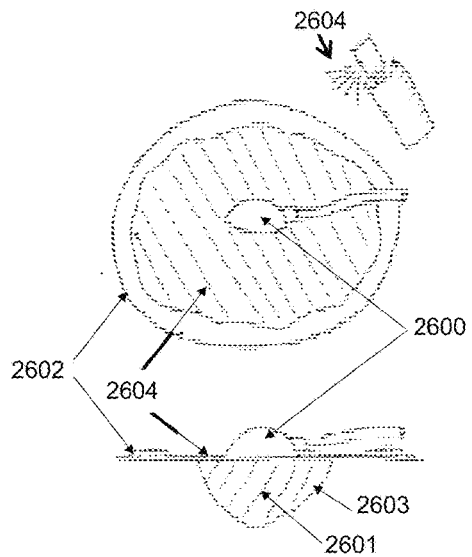
Figure 26C:
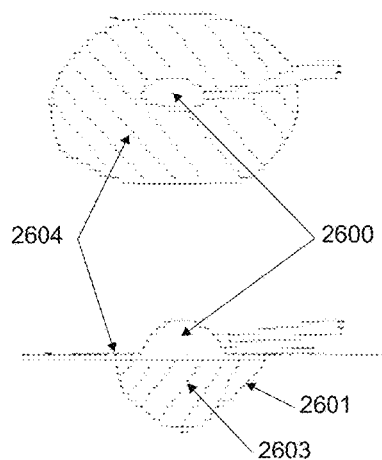

FIGS. 26A to 26C illustrate one example of a procedure and system that may be used to apply a spray-on or otherwise applied dressing over a wound with a drape or containment element to control the distribution of the dressing. First, a reduced pressure conduit 2600 is placed over a wound contact material 2601 and then a drape 2602 is placed around wound 2603. A spray sealant material 2604 over the wound 2603 and contact material 2601 with some coverage of the drape 2602. The drape 2602 is then removed and the sealant material 2604 is permitted to cure/set to form an air-tight barrier.

Figure 27:
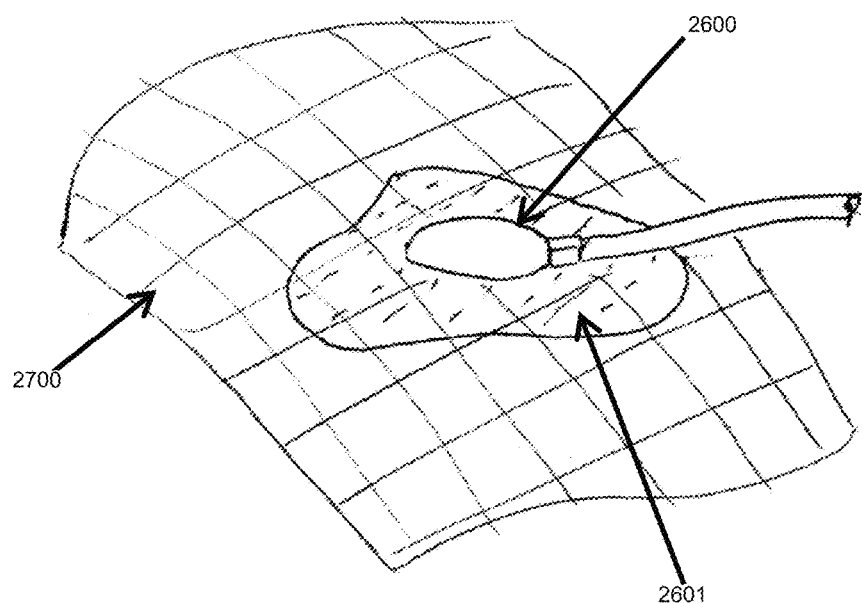
FIG. 27 is a schematic superior perspective view of a mesh-reinforced, liquid-sealed dressing.

FIG. 27 illustrate an optional structure and procedure that may be used with that depicted in FIGS. 26A to 26C, wherein a mesh or netting 2700 is applied after applying the contact material 2601 to the treatment site but either before (as depicted in FIG. 27) or after the spraying of the dressing. In some examples, applying the netting 2700 first may help to hold and/or capture the applied sealant, for example, by surface forces. The port 2600 may be placed on prior or after application of the dressing material to create a conduit between the reduced pressure source and the wound.

Figure 28:
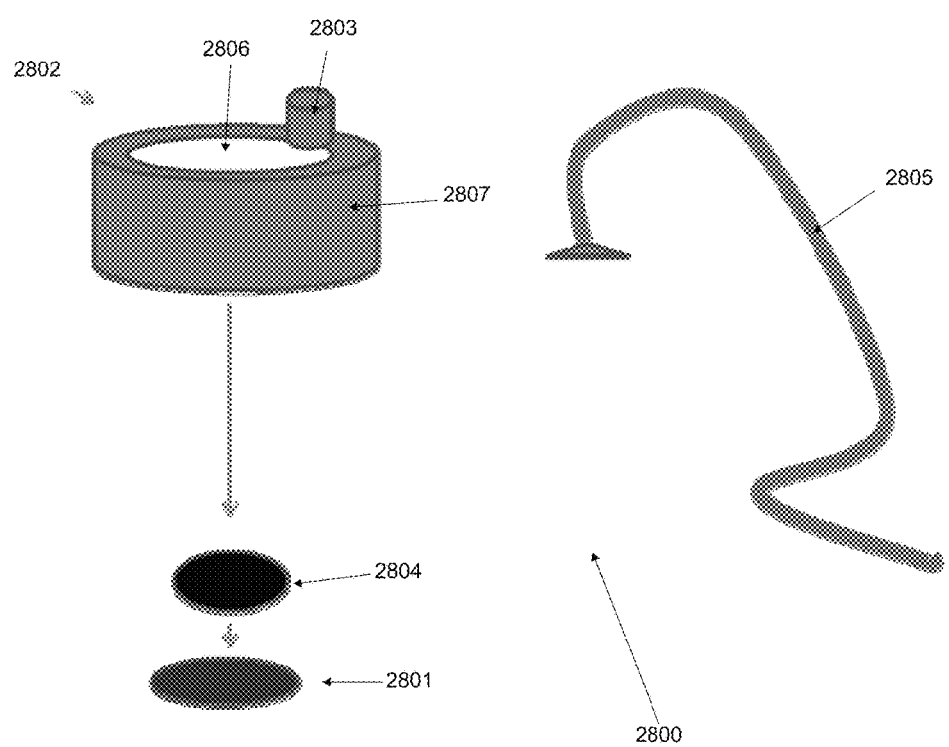
FIG. 28 depicts an example of a liquid-sealing system.

FIG. 28 illustrates another system 2800 configured to apply a spray-on sealant material to treatment site 2801, comprising a cuff 2802 with a RPWT conduit holder 2803. In use, after preparing the treatment site 2801, a wound contact material 2804 is applied to the treatment site 2801, then the cuff 2802 is placed around the treatment site 2801 and the port 2805 is positioned over the contact material 2804 and held in place by the port/tubing holder 2803. The sealant material is then sprayed into the opening or cavity 2806 of the cuff 2802 to seal the treatment site 2801 and the port 2805 to the treatment site 2801. Although the conduit holder 2803 is depicted as being located on the superior surface of the cuff 2802, in other variations, the conduit holder may be located on a side wall 2807 of the cuff 2802. Also, the cuff need not have the circular configuration as depicted in FIG. 28, and may have any of a variety of shapes, or may even be plastically deformable or malleable to provide a customized masking shape.

It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. For all the embodiments described herein, the steps of the method need not be performed sequentially.

What is claimed:

1. A device for providing reduced pressure treatment of a location on a patient, the device comprising:
    a cover structure comprising an upper surface, a lower surface and a first opening extending through the cover structure from the upper surface to the lower surface, wherein the first opening is capable of communicating with the location when the device engages with the patient; and
    a port assembly configured to fluidly couple to a negative pressure source, wherein the port assembly comprises:
    a first wall coupled to the upper surface of the cover structure and having a second opening in fluid communication with the first opening,
    a compliant second wall, and
    a volume formed between the first wall and the compliant second wall and in fluid communication with the negative pressure source, the volume capable of being in fluid communication with the location when the device engages with the patient,
    wherein the compliant second wall is biased to an expanded state upon exposure of the volume to atmospheric pressure and adapted to deform to a collapsed state if the volume is exposed to a negative pressure from the negative pressure source,
    wherein the first wall is configured not to collapse if the volume is exposed to the negative pressure, and
    wherein an upper surface of the first wall comprises a visually distinctive region, wherein the visually distinctive region transitions from a hidden state to a visible state and becomes visible through the compliant second wall when the compliant second wall transitions from the expanded state to the collapsed state, wherein when the visually distinctive region is in the hidden state, the compliant second wall obstructs a view of the visually distinctive region.

2. The device of claim 1, wherein the compliant second wall provides an indication of the negative pressure under the cover structure at the location.

3. The device of claim 2, wherein the compliant second wall provides an indication that the negative pressure under the cover structure at the location is lost.

4. The device of claim 1, wherein the exposure of the volume to negative pressure reduces the volume and deforms the compliant second wall to approach the first wall.

5. The device of claim 1, wherein the compliant second wall is translucent and the visually distinctive region is obscured by the compliant second wall in the expanded state.

6. The device of claim 1, wherein the visually distinctive region comprises at least one of a color, a pigment, a symbol, a pattern, or a text.

7. The device of claim 2, wherein the compliant second wall is a first color and the first wall is a second color such that contact between the compliant second wall and the first wall provides a visible indication of a presence of the negative pressure under the cover structure at the location.

8. The device of claim 1, wherein the location on the patient is at least in part external to a skin region of the patient.

9. The device of claim 1, wherein the location on the patient is at least in part internal to a skin region of the patient.

10. The device of claim 1, wherein the compliant second wall deforms from the expanded state to the collapsed state upon exposure of the volume to the negative pressure.

11. The device of claim 10, wherein a relative position of the compliant second wall between the expanded state and the collapsed state indicates an amount of negative pressure delivered to the location.

12. The device of claim 1, wherein the first wall is an interior wall and the compliant second wall is an exterior wall.

13. A device for providing reduced pressure treatment of a location on a patient, comprising:
  a cover structure comprising an upper surface, a lower surface, and an opening extending through the cover structure from the upper surface to the lower surface, wherein the opening is capable of communicating with the location when the device engages with the patient; and
  a pressure indicator fluidly coupled to the opening in the cover structure and comprising a visually distinctive region,
  wherein the pressure indicator is configured to fluidly communicate with a source of negative pressure and comprises, during use, at least a first expanded profile prior to exposure of the location to a negative pressure from the negative pressure source and at least a second persistent collapsed profile upon exposure of the location to the negative pressure,
  wherein the pressure indicator comprises a first wall configured not to collapse upon exposure of the location to the negative pressure, and
  wherein when the pressure indicator transitions from the first expanded profile to the second persistent collapsed profile, the visually distinct region transitions from a hidden state to a visible state and becomes visible through a compliant second wall of the pressure indicator, wherein when the visually distinctive region is in the hidden state, the compliant second wall obstructs a view of the visually distinctive region, and wherein when the pressure indicator transitions from the second persistent collapsed profile to the first expanded profile, the visually distinctive region transitions from the visible state to the hidden state.

14. The device of claim 13, wherein a volume of an interior space of the pressure indicator is greater when the pressure indicator is in the first expanded profile than the volume of the interior space when the pressure indicator is in the second persistent collapsed profile.

15. The device of claim 13, wherein the first expanded profile of the pressure indicator is convex and the second persistent collapsed profile of the pressure indicator is concave.

16. The device of claim 13, wherein the pressure indicator comprises an elastomeric membrane coupled to at least a portion of the cover structure.

17. The device of claim 13, further comprising a port assembly fluidly coupled to the cover structure and the pressure indicator, wherein the port assembly is configured to deliver negative pressure from the negative pressure source to the location.

18. The device of claim 17, wherein the pressure indicator comprises an elastomeric membrane surrounding at least a portion of the port assembly.

19. The device of claim 17, further comprising tubing coupled to the port assembly at a first end and coupled to the negative pressure source at an opposite end, wherein the tubing comprises a sidewall having at least one sidewall opening.

20. The device of claim 19, wherein the pressure indicator comprises an elastomeric membrane surrounding the at least one sidewall opening of the tubing.

21. The device of claim 13, wherein the pressure indicator comprises an internal space configured to be reduced upon exposure of the location to the negative pressure and to move the pressure indicator from the first expanded profile to the second persistent collapsed profile.

22. The device of claim 13, wherein a relative position of the pressure indicator between the first expanded profile and the second persistent collapsed profile is indicative of an amount of negative pressure delivered to the location.

23. The device of claim 13, wherein the location on the patient is at least in part external to a skin region of the patient.

24. The device of claim 13, wherein the location on the patient is at least in part internal to a skin region of the patient.

25. The device of claim 1, wherein the volume is capable of being in fluid communication with the location through the first opening and the second opening when the device engages with the patient.

26. The device of claim 1, wherein the port assembly is configured to fluidly couple the negative pressure source with the location through the first opening, the second opening, and the volume when the device engages with the patient.

27. The device of claim 1, wherein the first wall is beneath the compliant second wall.

* * * * *